US012612431B2

(12) United States Patent
Cai et al.

(10) Patent No.: US 12,612,431 B2
(45) **Date of Patent: *Apr. 28, 2026**

(54) CYCLIC COMPOUNDS FOR TREATING CANCER

(71) Applicant: University of South Florida, Tampa, FL (US)

(72) Inventors: Jianfeng Cai, Tampa, FL (US); Mengmeng Zheng, Brighton, MA (US)

(73) Assignee: University of South Florida, Tampa, FL (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/838,028

(22) Filed: Jun. 10, 2022

(65) Prior Publication Data

US 2023/0042837 A1 Feb. 9, 2023

Related U.S. Application Data

(60) Provisional application No. 63/313,546, filed on Feb. 24, 2022, provisional application No. 63/202,564, filed on Jun. 16, 2021.

(51) Int. Cl.

*C07K 7/56* (2006.01)
*A61P 35/00* (2006.01)
*A61K 38/00* (2006.01)

(52) U.S. Cl.

CPC ................ *C07K 7/56* (2013.01); *A61P 35/00* (2018.01); *A61K 38/00* (2013.01)

(58) Field of Classification Search

None

See application file for complete search history.

(56) References Cited

U.S. PATENT DOCUMENTS

| | | | | |
|---|---|---|---|---|
| 10,738,082 | B2 * | 8/2020 | Cai | A61K 38/00 |
| 11,149,065 | B2 * | 10/2021 | Cai | C07K 1/047 |
| 11,214,835 | B1 * | 1/2022 | Patel | A61K 31/404 |
| 11,278,521 | B2 * | 3/2022 | Patel | A61K 45/06 |
| 2022/0195524 | A1 * | 6/2022 | Patel | A61K 31/404 |
| 2023/0008571 | A1 | 1/2023 | Cai et al. | |

FOREIGN PATENT DOCUMENTS

| | | | |
|---|---|---|---|
| WO | WO2017106505 A1 * | 6/2017 | A61K 31/38 |

OTHER PUBLICATIONS

Shi et al. One-Bead-Two-Compound Thioether Bridged Macrocyclic γ-AApeptide Screening Library against EphA2. J. Med. Chem. 2017, 60, 9290-9298. (Year: 2017).*

Bujard et al., "HDM-PAMPA to predict gastrointestinal absorption, binding percentage, equilibrium and kinetics constants with human serum albumin and using 2 end-point measurements," European Journal of Pharmaceutical Sciences, Jan. 15, 2017, 97:143-150.

Di et al., "High throughput artificial membrane permeability assay for blood-brain barrier," European journal of medicinal chemistry, Mar. 1, 2003, 38(3):223-232.

Fallingborg J. Intraluminal pH of the human gastrointestinal tract. Danish medical bulletin. Jun. 1, 1999;46(3):183-196.

Fang et al., "Penetration of verapamil across blood brain barrier following cerebral ischemia depending on both paracellular pathway and P-glycoprotein transportation," Neurochemistry international, Jan. 1, 2013, 62(1):23-30.

Filipski et al., "Intestinal targeting of drugs: rational design approaches and challenges," Current Topics in Medicinal Chemistry, Apr. 1, 2013, 13(7):776-802.

Holbro et al., "ErbB receptors: directing key signaling networks throughout life," Annual review of pharmacology and toxicology, Feb. 10, 2004, 44(1):195-217.

Hynes et al., "ErbB receptors and signaling pathways in cancer," Current opinion in cell biology, Apr. 1, 2009, 21(2):177-184.

Jones et al., "Binding specificities and affinities of egf domains for ErbB receptors," FEBS letters, Mar. 26, 1999, 447(2-3):227-231.

Kodadek, "Development of antibody surrogates for the treatment of cancers and autoimmune disease," Current opinion in chemical biology, Dec. 1, 2010, 14(6):721-727.

Koehler et al., "Afatinib, erlotinib and gefitinib in the first-line therapy of EGFR mutation-positive lung adenocarcinoma: a review," Oncology Research and Treatment, 2013, 36(9):510-518.

Li et al., "Identification and characterization of a novel peptide ligand of epidermal growth factor receptor for targeted delivery of therapeutics," The FASEB journal, Dec. 2005, 19(14):1978-1985.

Li et al., "Structural basis for inhibition of the epidermal growth factor receptor by cetuximab," Cancer cell, Apr. 1, 2005, 7(4):301-311.

Liu et al., "Prediction of the blood-brain barrier (BBB) permeability of chemicals based on machine-learning and ensemble methods," Chemical Research in Toxicology, May 28, 2021, 34(6):1456-1467.

Madhavi Sastry et al., "Protein and ligand preparation: parameters, protocols, and influence on virtual screening enrichments," Journal of computer-aided molecular design, Mar. 2013, 27(3):221-234.

Mosesson et al., "Oncogenic growth factor receptors: implications for signal transduction therapy," InSeminars in cancer biology, Aug. 1, 2004, 14(4): 262-270.

Nicholas et al., "Epidermal growth factor receptor-mediated signal transduction in the development and therapy of gliomas," Clinical Cancer Research, Dec. 15, 2006, 12(24):7261-7270.

Ogiso et al., "Crystal structure of the complex of human epidermal growth factor and receptor extracellular domains," Cell, Sep. 20, 2002, 110(6):775-787.

Paez et al., "EGFR mutations in lung cancer: correlation with clinical response to gefitinib therapy," Science, Jun. 4, 2004, 304(5676):1497-1500.

Rocha-Lima et al., "EGFR targeting of solid tumors," Cancer control, Jul. 2007, 14(3):295-304.

(Continued)

*Primary Examiner* — Lianko G Garyu
*Assistant Examiner* — Jia-Hai Lee
(74) *Attorney, Agent, or Firm* — Michele L. Lawson; Shumaker, Loop & Kendrick, LLP

(57) ABSTRACT

Provided are cyclic peptidomimetics that can, e.g., antagonize the extracellular domain of EGFR, and methods of use thereof.

2 Claims, 15 Drawing Sheets

(56) References Cited

OTHER PUBLICATIONS

Rowinsky, "The erbB family: targets for therapeutic development against cancer and therapeutic strategies using monoclonal antibodies and tyrosine kinase inhibitors," Annual review of medicine, 2004, 55:433-457.
Sanders et al., "Molecular determinants of epidermal growth factor binding: a molecular dynamics study," PloS one, Jan. 24, 2013, 8(1):e54136, 12 pages.
Sang et al., "Inhibition of β-catenin/B cell lymphoma 9 protein—protein interaction using α-helix-mimicking sulfono-γ-AApeptide inhibitors," Proceedings of the National Academy of Sciences, May 28, 2019, 116(22):10757-10762.
Schmiedel et al., "Matuzumab binding to EGFR prevents the conformational rearrangement required for dimerization," Cancer cell, Apr. 8, 2008, 13(4):365-373.
Sharma et al., "Epidermal growth factor receptor mutations in lung cancer," Nature Reviews Cancer, Mar. 2007, 7(3):169-181.
She et al., "De Novo Left-Handed Synthetic Peptidomimetic Foldamers," Angewandte Chemie, Jul. 26, 2018, 130(31):10064-10068.
Shi et al., "One-bead-two-compound thioether bridged macrocyclic γ-AApeptide screening library against EphA2," Journal of medicinal chemistry, Nov. 22, 2017, 60(22):9290-9298.
Shi et al., "Stabilization of 1ncRNA GAS5 by a small molecule and its implications in diabetic adipocytes," Cell chemical biology, Mar. 21, 2019, 26(3):319-330.
Shi et al., "γ-AApeptides: Design, structure, and applications," Accounts of chemical research, Mar. 15, 2016, 49(3):428-441.
Song et al., "Novel peptide ligand directs liposomes toward EGF-R high-expressing cancer cells in vitro and in vivo," The FASEB Journal, May 2009, 23(5):1396-1404.
Teng et al., "Hydrogen-bonding-driven 3D supramolecular assembly of peptidomimetic zipper," Journal of the American Chemical Society, Mar. 28, 2018, 140(17):5661-5665.
Teng et al., "Identification of novel inhibitors that disrupt STAT3-DNA interaction from a γ-AApeptide OBOC combinatorial library," Chemical Communications, 2014, 50(63):8739-8742.
Teng et al., "Orthogonal Halogen-Bonding-Driven 3D Supramolecular Assembly of Right-Handed Synthetic Helical Peptides," Angewandte Chemie, Jun. 3, 2019, 131(23):7860-7864.
Teng et al., "Right-handed helical foldamers consisting of de novo d-Aapeptides," Journal of the American Chemical Society, May 31, 2017, 139(21):7363-7369.
Teng et al., "γ-AApeptides as a New Class of Peptidomimetics," Chemistry—A European Journal, Apr. 11, 2016, 22(16):5458-5466.
Udugamasooriya et al., "A peptoid "antibody surrogate" that antagonizes VEGF receptor 2 activity," Journal of the American Chemical Society, Apr. 30, 2008, 130(17):5744-5752.
Yan et al., "Cyclic peptidomimetics as inhibitor for miR-155 biogenesis," Molecular pharmaceutics, Jan. 2, 2019, 16(2):914-920.
Yarden et al., "Untangling the ErbB signalling network," Nature reviews Molecular cell biology, Feb. 2001, 2(2):127-137.
Yarden, "The EGFR family and its ligands in human cancer: signalling mechanisms and therapeutic opportunities," European journal of cancer, Sep. 1, 2001, 37:3-8.
Zhang et al., "An allosteric mechanism for activation of the kinase domain of epidermal growth factor receptor," Cell, Jun. 13, 2006, 125(6):1137-1149.
Zheng et al., "Discovery of Cyclic Peptidomimetic Ligands Targeting the Extracellular Domain of EGFR," Journal of Medicinal Chemistry, Jul. 23, 2021, 64(15):11219-11228.

* cited by examiner

FIG. 1A
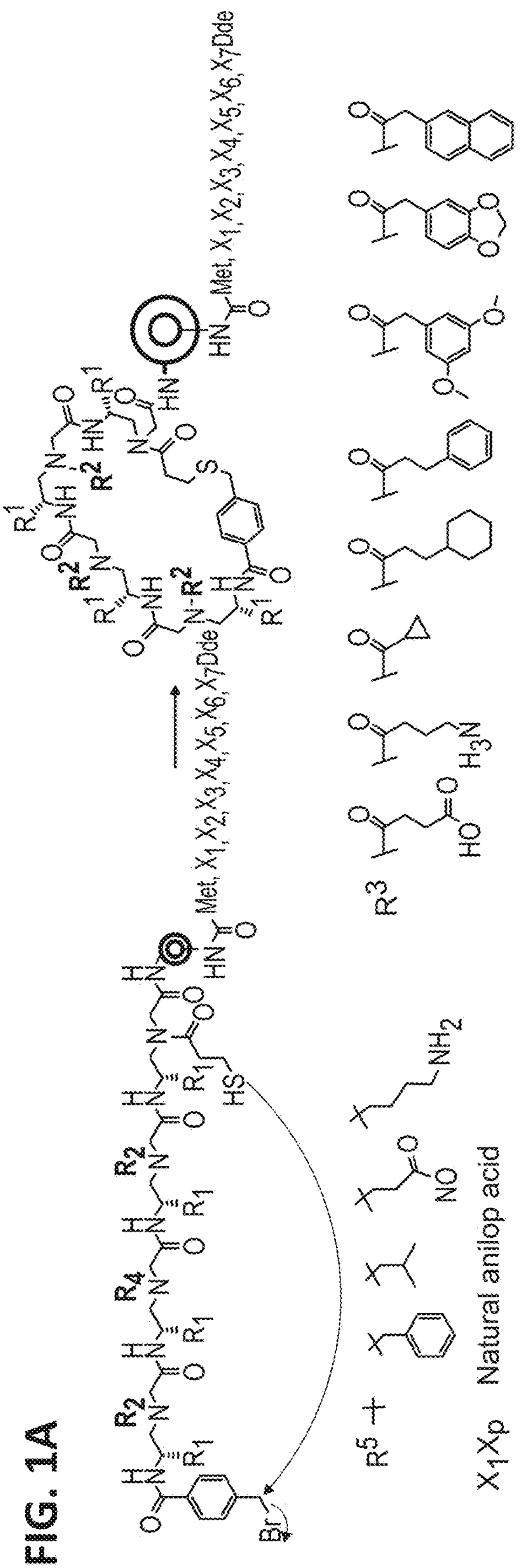
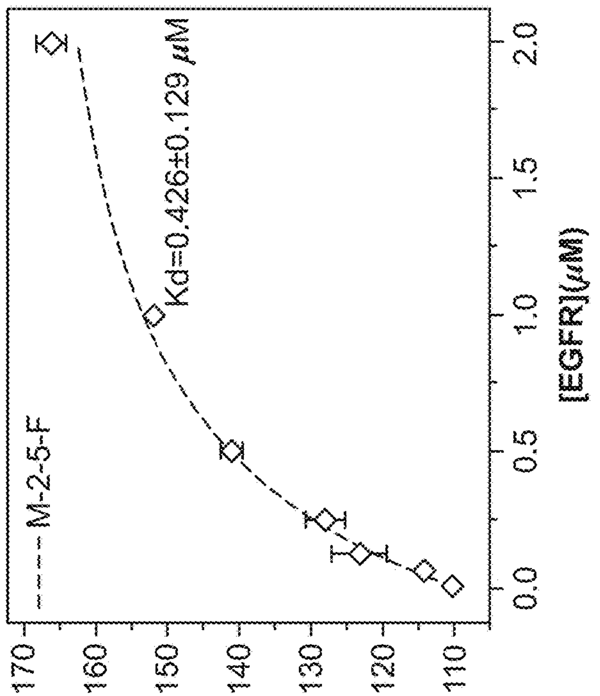
FIG. 1B

M-2-3-F

M-2-1-F

M-2-5-F

M-2-4-F

M-2-5

FIG. 9A
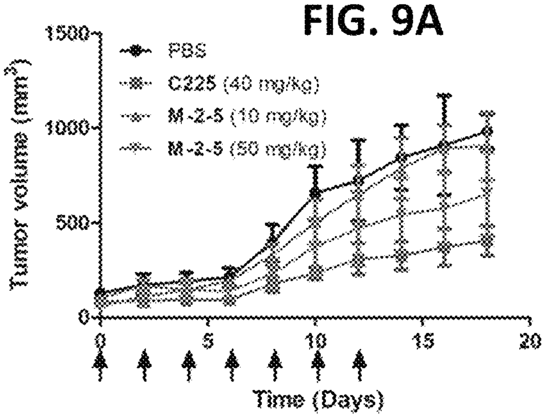
FIG. 9B
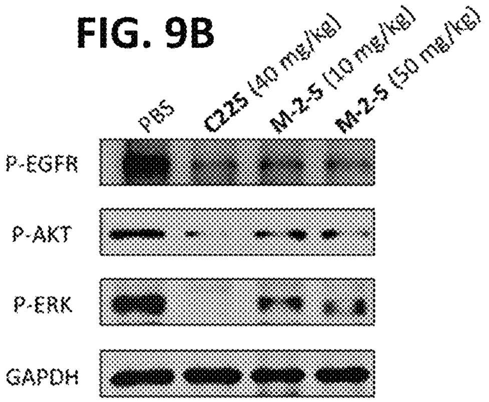
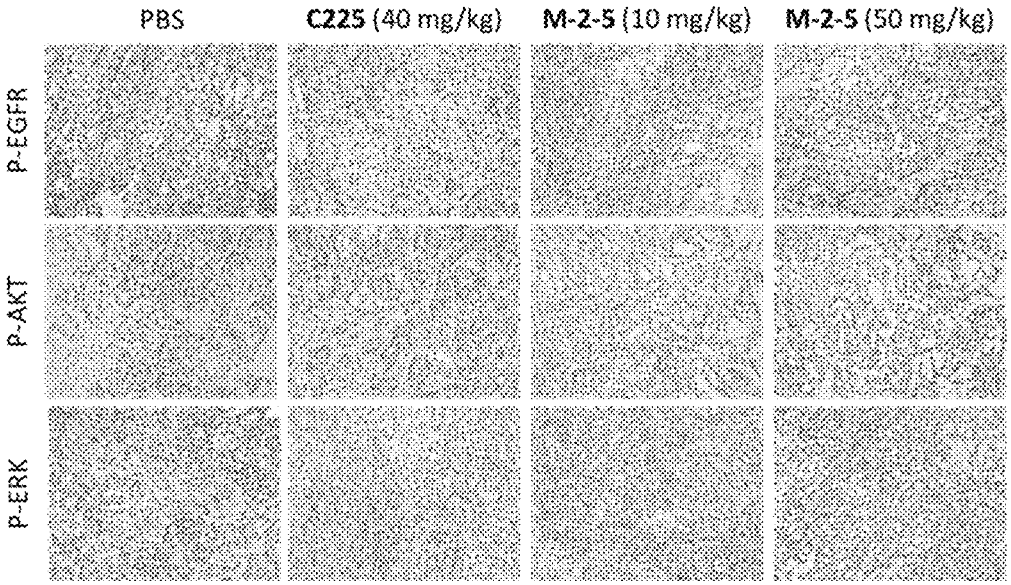
FIG. 9C

CYCLIC COMPOUNDS FOR TREATING CANCER

CROSS-REFERENCE TO RELATED APPLICATIONS

This application claims priority to U.S. Provisional Application No. 63/202,564, filed on Jun. 16, 2021; and U.S. Provisional Application No. 63/313,546, filed on Feb. 24, 2022; which are incorporated by reference herein in their entirety.

TECHNICAL FIELD

Provided are cyclic peptidomimetic compounds that can be used for, e.g., treating EGFR-associated cancers.

BACKGROUND

As a member of the receptor tyrosine kinase family, epidermal growth factor receptor (EGFR) plays a role in the control of cellular transduction pathways and regulation of growth and differentiation of many cell types. Previous studies suggest that EGFR is abnormally expressed in a variety of human epithelial malignancies, such as glioma, lung cancer, and colon cancer, and therefore has been used as a target for the development of drugs for the treatment of cancers that may be caused by epidermal growth factor receptor up-regulation.

EGFR, also known as ErbB-1, is a transmembrane receptor which has an extracellular ligand-binding domain, a transmembrane domain and an intracellular tyrosine kinase domain. As such, the small molecules targeting the intracellular tyrosine kinase domain and monoclonal antibodies that bind to the extracellular domain of EGFR are the two main approaches currently undertaken to inhibit EGFR functions for cancer therapy. However, small molecule EGFR inhibitors such as erlotinib, gefitinib, and afatinib, which are known to target the intracellular catalytic domain of EGFR tyrosine kinase thereby inhibiting EGFR phosphorylation and downstream signaling, lead to intrinsic or acquired resistance rapidly. Meanwhile, these small tyrosine kinase inhibitors lack specificity and as a result they generally exhibit severe toxic side effects, limiting the prolonged use of these drugs in clinical therapy. Further, anti-EGFR monoclonal antibodies, such as cetuximab and matuzumab, which could recognize the extracellular domain of EGFR exclusively with high affinity and specificity, have already been successfully developed for clinical therapeutic strategies.

Despite the success of EGFR-targeted drugs, there are high demands for EGFR therapeutics with lower cost and improved efficacy. Peptides that bind to the extracellular domain of EGFR have been developed through phage display or virtual screening, however, they were subsequently investigated as EGFR targeting ligands, whereas their own ability to mimic monoclonal antibody and affect EGFR signaling was not reported. Meanwhile, the peptides are susceptible to rapid proteolytic degradation. The strategy described herein takes advantage of peptidomimetics that mimic structure and function of peptides.

SUMMARY

Accordingly, in one aspect, provided herein are compounds of formula (I), or a pharmaceutically acceptable salt thereof

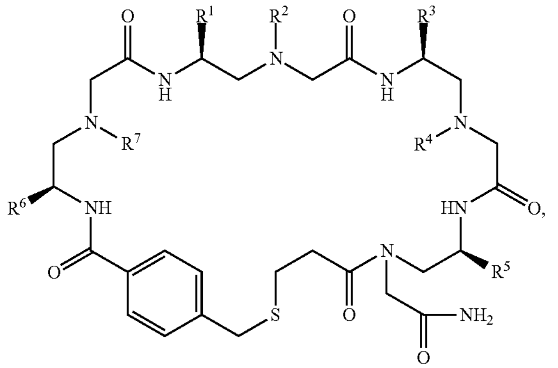

or pharmaceutically acceptable salts thereof, wherein $R^1$, $R^2$, $R^3$, $R^4$, $R^5$, $R^6$, and $R^7$ are as defined herein.

Disclosed herein is a method of treating cancer in a subject in need thereof, comprising administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method of treating an EGFR-associated cancer in a subject in need thereof, comprising administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method for treating cancer in a subject in need thereof, comprising:

(a) determining if the cancer is associated with a dysregulation of an EGFR receptor, or expression or activity or level of any of the same; and (b) if the cancer is determined to be associated with a dysregulation of an EGFR receptor, or expression or activity or level of any of the same, administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method for treating an EGFR-associated cancer in a subject in need thereof, comprising:

(a) determining if the cancer is associated with a dysregulation of an EGFR receptor, or expression or activity or level of any of the same; and (b) if the cancer is determined to be associated with a dysregulation of an EGFR receptor, or expression or activity or level of any of the same, administering to the subject an effective amount of a compound of Formula (I) or a pharmaceutically acceptable salt thereof, or a pharmaceutical composition comprising a compound of Formula (I) or a pharmaceutically acceptable salt thereof, to a subject having a clinical record that indicates that the subject has a dysregulation of an EGFR receptor, or expression or activity or level of any of the same. Disclosed herein is a method of treating a subject, the method comprising administering a therapeutically effective amount of a compound of Formula (I) or a pharmaceutically acceptable salt thereof, or a pharmaceutical composition comprising a compound of Formula (I) or a pharmaceutically acceptable salt thereof.

Disclosed herein is a method for inhibiting metastasis in a subject having cancer in need of such treatment, comprising administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method for inhibiting tumorigenesis in a subject having cancer in need of such treatment, comprising administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method for inhibiting mammalian cell proliferation, comprising contacting the mammalian cell with a compound of Formula (I) or a pharmaceutically acceptable salt thereof.

Disclosed herein is a method for inhibiting EGFR receptor activity in a mammalian cell, comprising contacting the mammalian cell with a compound of Formula (I) or a pharmaceutically acceptable salt thereof.

Disclosed herein is a method for inhibiting EGFR phosphorylation in a mammalian cell, comprising contacting the mammalian cell with a compound of Formula (I) or a pharmaceutically acceptable salt thereof.

Other aspects of the disclosure will become apparent by consideration of the detailed description and accompanying drawings.

BRIEF DESCRIPTION OF THE DRAWINGS

FIG. 1A is a scheme depicting the synthesis of a cyclic γ-AApeptides library. FIG. 1B is a plot of the binding affinity of M-2-5-F to EGFR measured by a fluorescence polarization (FP) assay.

FIG. 9A is a plot depicting time course assessment of total tumor volume. The day when treatment started was recorded as day 0 and arrows indicate the time of injection. Tumor volume was measured once every 2 days until day 18. FIG. 9B is a western blot analysis of phosphor-EGFR and downstream signaling pathway in tumor lysates. GAPDH was used as a loading control. FIG. 9C shows immunohistochemical staining for P-EGFR, P-AKT and P-ERK. Representative staining of section from A549 tumors with antibodies against the indicated proteins.

Figure 2:
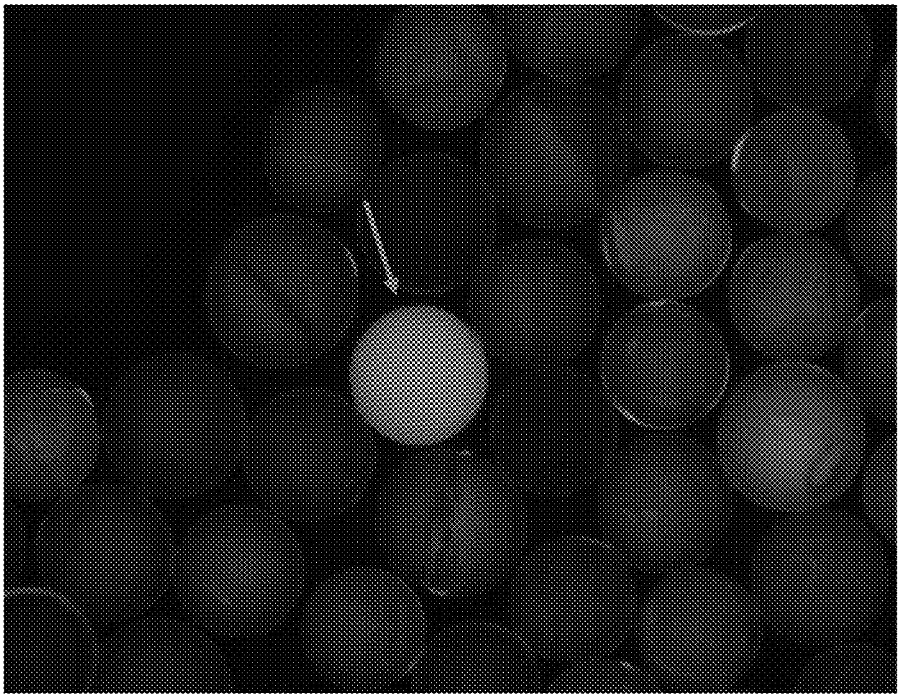
FIG. 2 is a representative image of beads for screening.

Before any embodiments of the disclosure are explained in detail, it is to be understood that the disclosure is not limited in its application to the details of construction and the arrangement of components set forth in the following description or illustrated in the accompanying drawings. The disclosure is capable of other embodiments and of being practiced or of being carried out in various ways.

DETAILED DESCRIPTION

Herein are provided cyclic peptidomimetics, produced from a one-bead-two-compound (OBTC) library that contains 320,000 cyclic γ-AApeptides. The compound M-2-5, obtained from this library, was found to tightly bind to the extracellular domain of EGFR. M-2-5 also antagonized EGF stimulated EGFR phosphorylation and downstream signal transduction. Furthermore, together with its resistance to proteolytic degradation, M-2-5 was shown to inhibit cell proliferation and migration in vitro and suppress tumor growth in A549 xenograft models in vivo, implying its therapeutic potential for the treatment of cancer.

Definitions

The use of "including," "comprising," or "having" and variations thereof herein is meant to encompass the items listed thereafter and equivalents thereof as well as additional items. Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* $3^{rd}$ Edition, Cambridge University Press, Cambridge, 1987; the entire contents of each of which are incorporated herein by reference.

The term "compound," as used herein is meant to include all stereoisomers, geometric isomers, tautomers, and isotopically enriched variants of the structures depicted. Compounds herein identified by name or structure as one particular tautomeric form are intended to include other tautomeric forms unless otherwise specified.

The term "C1-C6 alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Similarly, a C1-C3 alkyl group is linear or branched hydrocarbon chain containing 1, 2, or 3 carbon atoms.

The term "C1-C6 alkoxy" refers to a C1-C6 alkyl group which is attached to a molecule via oxygen. This includes moieties where the alkyl part may be linear or branched, such as methoxy, ethoxy, n-propoxy, iso-propoxy, n-butoxy, sec-butoxy, tert-butoxy, n-pentoxy and n-hexoxy.

As used herein, the term "aryl" refers to a 6-10 all carbon mono- or fused bicyclic group wherein at least one ring in the system is aromatic. Non-limiting examples of aryl groups include phenyl, naphthyl, tetrahydronaphthyl. In bicyclic ring systems where only one ring is aromatic, the non-aromatic ring can be a cycloalkyl group, as defined herein.

As used herein, the term "cycloalkyl" refers to a saturated or partially unsaturated 3-10 mono- or bicyclic hydrocarbon group; wherein bicyclic systems include fused, spiro (optionally referred to as "spirocycloalkyl" groups), and bridged ring systems. In bicyclic ring systems, one ring can be aromatic, and the other ring can be saturated or partially unsaturated, so long as the bicyclic ring system is not aromatic. Non-limiting examples of cycloalkyl groups include cyclopropyl, cyclohexyl, spiro[2.3]hexyl, bicyclo[1.1.1]pentyl, tetrahydronaphthalenyl, and decahydronaphthalenyl.

The term "heterocyclyl" refers to a fully or partially unsaturated 3-12 membered hydrocarbon monocyclic or bicyclic ring system, that is not aromatic (but that can include an aromatic ring as part of a bicyclic ring system), having at least one heteroatom within the ring selected from N, O and S. Bicyclic heterocyclyl groups include fused, spiro (optionally referred to as "spiroheterocyclyl" groups), and bridged ring systems. The heterocyclyl ring system may include oxo substitution at one or more C, N, or S ring members. The heterocyclyl group may be denoted as, for example, a "5-10 membered heterocyclyl group," which is a ring system containing 5, 6, 7, 8, 9 or 10 atoms at least one being a heteroatom. For example, there may be 1, 2 or 3 heteroatoms, optionally 1 or 2. The heterocyclyl group may be bonded to the rest of the molecule through any carbon atom or through a heteroatom such as nitrogen. In bicyclic ring systems, one ring can be aromatic, and the other ring can be saturated or partially unsaturated, so long as the bicyclic ring system is not aromatic. Exemplary heterocyclyl groups include, but are not limited to, aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,4-dioxolanyl, 1,3-oxathianyl, 1,4-oxathiinyl, 1,3-oxathiolanyl, 1,3-dithiolyl, 1,3-dithiolanyl, 1,4-oxathianyl, tetrahydro-1,4-thiazinyl, 2H-1,2-oxazinyl, maleimidyl, succinimidyl, dioxopiperazinyl, hydantoinyl, imidazolinyl, imidazolidinyl, isoxazolinyl, isoxazolidinyl, isoindolinyl, indolinyl, oxazolinyl, oxazolidinyl, oxazolidinonyl, thiazolinyl, thiazolidinyl, morpholinyl, oxiranyl, piperidinyl N-oxide, piperidinyl, piperazinyl, pyrrolidinyl, pyrrolidonyl, pyrrolidionyl, 4-piperidonyl, pyrazolinyl, pyrazolidinyl, 2-oxopyrrolidinyl, tetrahydropyranyl, 4H-pyranyl, tetrahydrothiopyranyl, 1,4-diazabicyclo[2.2.2]octane, 1,4-diazabicyclo[3.1.1]heptane, 2-azaspiro[3,3]heptane, 2,6-diazaspiro[3,3]heptane, 2-oxa-6-azaspiro[3,3]heptane, benzimidazolidinonyl, tetrahydroquinolinyl, and 3,4-methylenedioxyphenyl.

As used herein, the symbol depicts the point of attachment of an atom or moiety to the indicated atom or group in the remainder of the molecule.

The compounds of Formula (I) include pharmaceutically acceptable salts thereof. In addition, the compounds of Formula (I) also include other salts of such compounds which are not necessarily pharmaceutically acceptable salts, and which may be useful as intermediates for preparing and/or purifying compounds of Formula (I) and/or for separating enantiomers of compounds of Formula (I). Non-limiting examples of pharmaceutically acceptable salts of compounds of Formula (I) include trifluoroacetic acid and hydrochloride salts.

It will further be appreciated that the compounds of Formula (I) or their salts may be isolated in the form of solvates, and accordingly that any such solvate is included within the scope of the present disclosure. For example, compounds of Formula (I) and salts thereof can exist in unsolvated as well as solvated forms with pharmaceutically acceptable solvents such as water, ethanol, and the like.

The term "pharmaceutically acceptable" indicates that the compound, or salt or composition thereof is compatible chemically and/or toxicologically with the other ingredients comprising a formulation and/or the subject being treated therewith. The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

Compounds provided herein may also contain unnatural proportions of atomic isotopes at one or more of the atoms that constitute such compounds. That is, an atom, in particular when mentioned in relation to a compound according to Formula (I), comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof; unless expressly noted otherwise. For example, in deuteroalkyl and deuteroalkoxy groups, where one or more hydrogen atoms are specifically replaced with deuterium ($^{2}H$). As some of the aforementioned isotopes are radioactive, the compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present disclosure.

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 nonhydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 nonhydrogen radical.

For illustrative purposes, general methods for preparing the compounds are provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

As used herein, "treat", "treatment", "treating", and the like refer to acting upon a condition with an agent to affect the condition by improving or altering it. The condition includes, but is not limited to cancer. The agent includes, but is not limited to, compounds capable of inhibiting or preventing tumorigenesis, metastasis, and/or cancer cell migration. For example, the agent may include a compound described herein. The improvement or alteration may include an improvement in symptoms or an alteration in the physiologic pathways associated with the condition. The aforementioned terms cover one or more treatments of a condition in a subject (e.g., a mammal, typically a human or non-human animal of veterinary interest), and include: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reducing or eliminating the infection).

As used herein, the term "subject" includes humans and mammals (e.g., mice, rats, pigs, cats, dogs, and horses). Typical subjects to which an agent(s) of the present disclosure may be administered may include mammals, particularly primates, especially humans. For veterinary applications, suitable subjects may include, for example, livestock such as cattle, sheep, goats, cows, swine, and the like; poultry such as chickens, ducks, geese, turkeys, and the like; and domesticated animals particularly pets such as dogs and cats. For diagnostic or research applications, suitable subjects may include mammals, such as rodents (e.g., mice, rats, hamsters), rabbits, primates, and swine such as inbred pigs and the like. The subject may be immunocompromised. The subject may be immunosuppressed.

The "therapeutically effective amount" for purposes herein may be determined by such considerations as are known in the art. A therapeutically effective amount of an agent (such as a compound disclosed herein) may include the amount necessary to provide a therapeutically effective result in vivo. The amount of the compounds must be effective to achieve a response, including but not limited to a total prevention of (e.g., protection against) of a condition, improved survival rate or more rapid recovery, improvement or elimination of symptoms associated with the condition (such as and EGFR-associated cancer), or other indicators as are selected as appropriate measures by those skilled in the art. As used herein, a suitable single dose size includes a dose that is capable of preventing or alleviating (reducing or eliminating) a symptom in a subject when administered one or more times over a suitable time period. The "therapeutically effective amount" of a compound as described herein may depend on the route of administration, type of subject being treated, and the physical characteristics of the subject. These factors and their relationship to dose are well known to one of skill in the medicinal art, unless otherwise indicated.

As used herein, the term "$IC_{50}$" quantifies the ability of a compound to inhibit a specific biological or biochemical function. The $IC_{50}$ may, for example, refer to the concentration of a compound that inhibits EGF stimulation of EGFR phosphorylation by 50%.

The terms "administration" or "administering" as used herein may include the process in which the agents or compounds as described herein, alone or in combination with other agents or compounds, are delivered to a subject. The composition may be administered in various routes including, but not limited to, oral, parenteral (including intravenous, intra-arterial, and other appropriate parenteral routes), intrathecally, intramuscularly, subcutaneously, colonically, rectally, and nasally, transcutaneously, among others. Each of these conditions may be readily treated using other administration routes of compounds of the present disclosure. The dosing of the agents, compounds, and compositions described herein to obtain a therapeutic or prophylactic effect may be determined by the circumstances of the subject, as known in the art. The dosing of a subject herein may be accomplished through individual or unit doses of the compounds or compositions herein or by a combined or prepackaged or pre-formulated dose of a compounds or compositions.

Administration may depend upon the amount of compound administered, the number of doses, and duration of treatment. For example, multiple doses of the agent may be administered. The frequency of administration of the compound may vary depending on any of a variety of factors, such as extent of anxiety-related behavior, and the like. The duration of administration of the compound, e.g., the period of time over which the compound is administered, may vary, depending on any of a variety of factors, including subject response, etc.

The amount of the agent or compound contacted (e.g., administered) may vary according to factors such as the degree of susceptibility of the individual, the age, sex, and weight of the individual, idiosyncratic responses of the individual, the dosimetry, and the like. Detectably effective amounts of the agent or compound of the present disclosure may also vary.

Compounds

In one aspect, disclosed herein are compound of Formula (I), or a pharmaceutically acceptable salt thereof:

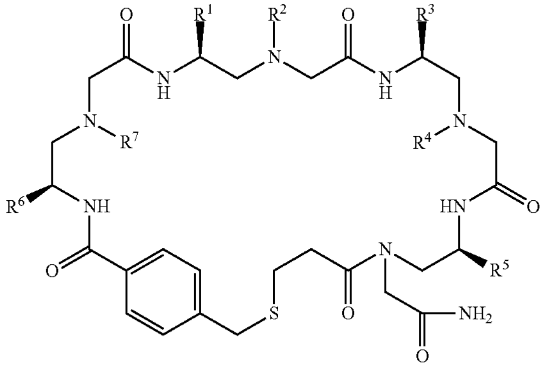

wherein:

$R^1$, $R^3$, and $R^5$ are each an independently selected C1-C6 alkyl optionally substituted with C6-C10 aryl, —$NR^BR^C$, or —C(═O)$OR^D$;

$R^6$ is C1-C6 alkyl substituted with C6-C10 aryl, —$NR^BR^C$, or —C(═O)$OR^D$;

$R^2$, $R^4$, and $R^7$ are each —C(═O)$R^A$;

each occurrence of $R^A$ is an independently selected C1-C6 alkyl optionally substituted with 1-2 substituents independently selected from C3-C6 cycloalkyl; C6-C10 aryl optionally substituted with 1-2 independently selected C1-C6 alkoxy; 3-9 membered heterocyclyl; —$NR^ER^F$; or —C(═O)$OR^G$; and each occurrence of $R^B$, $R^C$, $R^D$, $R^E$, $R^F$, and $R^G$ is independently selected from hydrogen and C1-C6 alkyl.

In some embodiments, $R^1$ is C1-C6 alkyl substituted with C6-C10 aryl, —$NR^BR^C$, or —C(═O)$OR^D$. In some embodiments, $R^1$ is C1-C6 alkyl optionally substituted with —$NR^BR^C$ or —C(═O)$OR^D$. In some embodiments, $R^1$ is C1-C6 alkyl substituted with —$NR^BR^C$ or —C(═O)$OR^D$. In some embodiments, $R^1$ is C1-C6 alkyl optionally substituted with —$NR^BR^C$ or C6-C10 aryl. In some embodiments, $R^1$ is C1-C6 alkyl substituted with —$NR^BR^C$ or C6-C10 aryl. In some embodiments, $R^1$ is C1-C6 alkyl substituted with C6-C10 aryl. In some embodiments, $R^1$ is C1-C6 alkyl optionally substituted with —$NR^BR^C$ or C(═O)$OR^D$. In some embodiments, $R^1$ is C1-C6 alkyl substituted with —$NR^BR^C$ or C(═O)$OR^D$. In some embodiments, $R^1$ is C1-C6 alkyl substituted with phenyl. In some embodiments, $R^1$ is methyl substituted with C6-C10 aryl. In some embodiments, $R^1$ is phenylmethyl. In some embodiments, $R^1$ is phenylethyl. In some embodiments, $R^1$ is C1-C6 alkyl substituted with —$NR^BR^C$. In some embodiments, $R^B$ and $R^C$ are each hydrogen. In some embodiments, —$NR^BR^C$ is —$NH_2$. In some embodiments, one of $R^B$ and $R^C$ is hydrogen and the other of $R^B$ and $R^C$ is C1-C6 alkyl. In some embodiments, one of $R^B$ and $R^C$ is hydrogen and the other of $R^B$ and $R^C$ is methyl. In some embodiments, —$NR^BR^C$ is —NHMe. In some embodiments, $R^B$ and $R^C$ are each independently selected C1-C6 alkyl. In some embodiments, $R^B$ and $R^C$ are each methyl. In some embodiments, —$NR^BR^C$ is —$NMe_2$. In some embodiments, $R^1$ is aminobutyl (e.g., 4-aminobutyl). In some embodiments, $R^1$ is C1-C6 alkyl substituted with —C(═O)$OR^D$. In some embodiments, $R^D$ is hydrogen. In some embodiments, $R^D$ is C1-C6 alkyl. In some embodiments, —C(═O)$OR^D$ is —C(═O)OH. In some embodiments, $R^D$ is t-butyl. In some embodiments, —C(═O)$OR^D$ is —C(═O)Ot-Bu. In some embodiments, $R^1$ is unsubstituted C1-C6 alkyl. In some embodiments, the $R^1$ C1-C6 alkyl is methyl, n-butyl, or isobutyl. In some embodiments, the $R^1$ C1-C6 alkyl is methyl. In some embodiments, the $R^1$ C1-C6 alkyl is n-butyl. In some embodiments, the $R^1$ C1-C6 alkyl is isobutyl.

In some embodiments, $R^3$ is C1-C6 alkyl substituted with C6-C10 aryl, —$NR^BR^C$, or —C(═O)$OR^D$. In some embodiments, $R^3$ is C1-C6 alkyl optionally substituted with —$NR^BR^C$ or —C(═O)$OR^D$. In some embodiments, $R^3$ is C1-C6 alkyl substituted with —$NR^BR^C$ or —C(═O)$OR^D$. In some embodiments, $R^3$ is C1-C6 alkyl optionally substituted with —$NR^BR^C$ or C6-C10 aryl. In some embodiments, $R^3$ is C1-C6 alkyl substituted with —$NR^BR^C$ or C6-C10 aryl. In some embodiments, $R^3$ is C1-C6 alkyl substituted with C6-C10 aryl. In some embodiments, $R^3$ is C1-C6 alkyl optionally substituted with —$NR^BR^C$ or C(═O)$OR^D$. In some embodiments, $R^3$ is C1-C6 alkyl substituted with —$NR^BR^C$ or C(═O)$OR^D$. In some embodiments, $R^3$ is C1-C6 alkyl substituted with phenyl. In some embodiments, $R^3$ is methyl substituted with C6-C10 aryl. In some embodiments, $R^3$ is phenylmethyl. In some embodiments, $R^3$ is phenylethyl. In some embodiments, $R^3$ is C1-C6 alkyl substituted with —$NR^BR^C$. In some embodiments, $R^B$ and $R^C$ are each hydrogen. In some embodiments, —$NR^BR^C$ is —$NH_2$. In some embodiments, one of $R^B$ and $R^C$ is hydrogen and the other of $R^B$ and $R^C$ is C1-C6 alkyl. In some embodiments, one of $R^B$ and $R^C$ is hydrogen and the other of $R^B$ and $R^C$ is methyl. In some embodiments, —$NR^BR^C$ is —NHMe. In some embodiments, $R^B$ and $R^C$ are each independently selected C1-C6 alkyl. In some embodiments, $R^B$ and $R^C$ are each methyl. In some embodiments, —$NR^BR^C$ is —$NMe_2$. In some embodiments, $R^3$ is aminobutyl (e.g., 4-aminobutyl). In some embodiments, $R^3$ is C1-C6 alkyl substituted with —C(═O)$OR^D$. In some embodiments, $R^D$ is hydrogen. In some embodiments, $R^D$ is C1-C6 alkyl. In some embodiments, —C(═O)$OR^D$ is —C(═O)OH. In some embodiments, $R^D$ is t-butyl. In some embodiments, —C(═O)$OR^D$ is —C(═O)Ot-Bu. In some embodiments, $R^3$ is unsubstituted C1-C6 alkyl. In some embodiments, the $R^3$ C1-C6 alkyl is methyl, n-butyl, or isobutyl. In some embodiments, the $R^3$ C1-C6 alkyl is methyl. In some embodiments, the $R^3$ C1-C6 alkyl is n-butyl. In some embodiments, the $R^3$ C1-C6 alkyl is isobutyl.

In some embodiments, $R^5$ is C1-C6 alkyl substituted with C6-C10 aryl, —$NR^BR^C$, or —C(═O)$OR^D$. In some embodiments, $R^5$ is C1-C6 alkyl optionally substituted with —$NR^BR^C$ or —C(═O)$OR^D$. In some embodiments, $R^5$ is C1-C6 alkyl substituted with —$NR^BR^C$ or —C(═O)$OR^D$. In some embodiments, $R^5$ is C1-C6 alkyl optionally substituted with —$NR^BR^C$ or C6-C10 aryl. In some embodiments, $R^5$ is C1-C6 alkyl substituted with —$NR^BR^C$ or C6-C10 aryl. In some embodiments, $R^5$ is C1-C6 alkyl substituted with C6-C10 aryl. In some embodiments, $R^5$ is C1-C6 alkyl optionally substituted with —$NR^BR^C$ or C(═O)$OR^D$. In some embodiments, $R^5$ is C1-C6 alkyl substituted with —$NR^BR^C$ or C(═O)$OR^D$. In some embodiments, $R^5$ is C1-C6 alkyl substituted with phenyl. In some embodiments, $R^5$ is methyl substituted with C6-C10 aryl. In some embodiments, $R^5$ is phenylmethyl. In some embodiments, $R^5$ is phenylethyl. In some embodiments, $R^5$ is C1-C6 alkyl substituted with —$NR^BR^C$. In some embodiments, $R^B$ and $R^C$ are each hydrogen. In some embodiments, —$NR^BR^C$ is —$NH_2$. In some embodiments, one of $R^B$ and $R^C$ is hydrogen and the other of $R^B$ and $R^C$ is C1-C6 alkyl. In some embodiments, one of $R^B$ and $R^C$ is hydrogen and the other of $R^B$ and $R^C$ is methyl. In some embodiments, —$NR^BR^C$ is —NHMe. In some embodiments, $R^B$ and $R^C$ are each independently selected C1-C6 alkyl. In some embodiments, $R^B$ and $R^C$ are each methyl. In some embodiments, —$NR^BR^C$ is —$NMe_2$. In some embodiments, $R^5$ is aminobutyl (e.g., 4-aminobutyl). In some embodiments, $R^5$ is C1-C6 alkyl substituted with —C(═O)$OR^D$. In some embodiments, $R^D$ is hydrogen. In some embodiments, $R^D$ is C1-C6 alkyl. In some embodiments, —C(═O)$OR^D$ is —C(═O)OH. In some embodiments, $R^D$ is t-butyl. In some embodiments, —C(═O)$OR^D$ is —C(═O)Ot-Bu. In some embodiments, $R^5$ is unsubstituted C1-C6 alkyl. In some embodiments, the $R^5$ C1-C6 alkyl is methyl, n-butyl, or isobutyl. In some embodiments, the $R^5$ C1-C6 alkyl is methyl. In some embodiments, the $R^5$ C1-C6 alkyl is n-butyl. In some embodiments, the $R^5$ C1-C6 alkyl is isobutyl.

In some embodiments, $R^6$ is C1-C6 alkyl substituted with C6-C10 aryl, —$NR^BR^C$, or —C(═O)$OR^D$. In some embodiments, $R^6$ is C1-C6 alkyl substituted with —$NR^BR^C$ or —C(═O)$OR^D$. In some embodiments, $R^6$ is C1-C6 alkyl substituted with —$NR^BR^C$ or C6-C10 aryl. In some embodiments, $R^6$ is C1-C6 alkyl optionally substituted with —$NR^BR^C$ or C(═O)$OR^D$. In some embodiments, $R^6$ is C1-C6 alkyl substituted with —$NR^BR^C$ or C(═O)$OR^D$. In some embodiments, $R^6$ is C1-C6 alkyl substituted with C6-C10 aryl. In some embodiments, $R^6$ is C1-C6 alkyl substituted with phenyl. In some embodiments, $R^6$ is methyl substituted with C6-C10 aryl. In some embodiments, $R^6$ is phenylmethyl. In some embodiments, $R^6$ is phenylethyl. In some embodiments, $R^6$ is C1-C6 alkyl substituted with —$NR^BR^C$. In some embodiments, $R^B$ and $R^C$ are each hydrogen. In some embodiments, —$NR^BR^C$ is —$NH_2$. In some embodiments, one of $R^B$ and $R^C$ is hydrogen and the other of $R^B$ and $R^C$ is C1-C6 alkyl. In some embodiments, one of $R^B$ and $R^C$ is hydrogen and the other of $R^B$ and $R^C$ is methyl. In some embodiments, —$NR^BR^C$ is —NHMe. In some embodiments, $R^B$ and $R^C$ are each independently selected C1-C6 alkyl. In some embodiments, $R^6$ is 4-aminobutyl. In some embodiments, $R^6$ is or

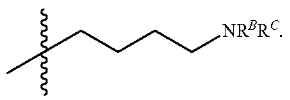

In some embodiments, $R^B$ and $R^C$ are each methyl. In some embodiments, $R^6$ is C1-C6 alkyl substituted with —C(═O)$OR^D$. In some embodiments, $R^D$ is hydrogen. In some embodiments, $R^D$ is C1-C6 alkyl. In some embodiments, —C(═O)$OR^D$ is —C(═O)OH. In some embodiments, $R^D$ is t-butyl. In some embodiments, —C(═O)$OR^D$ is —C(═O)Ot-Bu. In some embodiments, $R^6$ is C1-C6 alkyl substituted with —$CO_2H$. In some embodiments, $R^6$ is 4-carboxybutyl. In some embodiments, $R^6$ is

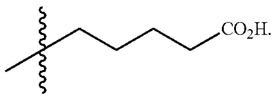 [SMILES: *CCCCC(=O)O]

In some embodiments, the $R^6$ C1-C6 alkyl is methyl, n-butyl, or isobutyl. In some embodiments, the $R^6$ C1-C6 alkyl is methyl. In some embodiments, the $R^6$ C1-C6 alkyl is n-butyl. In some embodiments, the $R^6$ C1-C6 alkyl is isobutyl.

In some embodiments, the $R^A$ of the $R^2$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy; 3-9 membered heterocyclyl; —$NR^ER^F$; or —C(═O)$OR^G$. In some embodiments, the $R^A$ of the $R^2$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy; 3-9 membered heterocyclyl; —$NR^ER^F$. In some embodiments, the $R^A$ of the $R^2$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy; 3-9 membered heterocyclyl. In some embodiments, the $R^A$ of the $R^2$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy. In some embodiments, the $R^A$ of the $R^2$—C(═O)$R^A$ is C1-C6 alkyl substituted with 1-2 substituents independently selected from C6-C10 aryl optionally substituted with 1-2 independently selected C1-C6 alkoxy; 3-9 membered heterocyclyl. In some embodiments, the $R^A$ of the $R^2$—C(═O)$R^A$ is C1-C6 alkyl substituted with 1-2 (e.g., 1) independently selected C3-C6 cycloalkyl. In some embodiments, the $R^A$ of the $R^2$—C(═O)$R^A$ is C1-C6 alkyl substituted with one C3-C6 cycloalkyl. In some embodiments, the $R^A$ of the $R^2$—C(═O)$R^A$ is ethyl substituted with one C3-C6 cycloalkyl. In some embodiments, the $R^A$ of the $R^2$—C(═O)$R^A$ is C1-C6 alkyl substituted with two C3-C6 cycloalkyl. In some embodiments, the $R^A$ of the $R^2$—C(═O)$R^A$ is C1-C6 alkyl substituted with cyclopropyl or cyclohexyl. In some embodiments, the $R^A$ of the $R^2$—C(═O)$R^A$ is C1-C6 alkyl substituted with one cyclohexyl. In some embodiments, the $R^A$ of the $R^2$—C(═O)$R^A$ is methyl substituted with C3-C6 cycloalkyl. In some embodiments, the $R^A$ of the $R^2$—C(═O)$R^A$ is cyclohexylmethyl. In some embodiments, the $R^A$ of the $R^2$—C(═O)$R^A$ is cyclohexylethyl. In some embodiments, the $R^A$ of the $R^2$—C(═O)$R^A$ is C1-C6 alkyl substituted with C6-C10 aryl optionally substituted with 1-2 independently selected C1-C6 alkoxy. In some embodiments, the $R^A$ of the $R^4$—C(═O)$R^A$ is C1-C6 alkyl substituted with C6-C10 aryl substituted with 1-2 independently selected C1-C6 alkoxy. In some embodiments, the $R^A$ of the $R^2$—C(═O)$R^A$ is methyl substituted with C6-C10 aryl optionally substituted with 1-2 independently selected C1-C6 alkoxy. In some embodiments, the $R^A$ of the $R^2$—C(═O)$R^A$ is C1-C6 alkyl substituted with phenyl optionally substituted with C1-C6 alkoxy. In some embodiments, the $R^A$ of the $R^2$—C(═O)$R^A$ is C1-C6 alkyl substituted with phenyl optionally substituted with 1-2 C1-C6 alkoxy. In some embodiments, the $R^A$ of the $R^2$—C(═O)$R^A$ is C1-C6 alkyl substituted with C6-C10 aryl optionally substituted with 1-2 methoxy. In some embodiments, the $R^A$ of the $R^2$—C(═O)$R^A$ is methyl substituted with C6-C10 aryl optionally substituted with 1-2 methoxy. In some embodiments, the $R^A$ of the $R^2$—C(═O)$R^A$ is C1-C6 alkyl substituted with phenyl optionally substituted with 1-2 methoxy. In some embodiments, the $R^A$ of the $R^2$—C(═O)$R^A$ is C1-C6 alkyl substituted with phenyl substituted with two methoxy. In some embodiments, the $R^A$ of the $R^2$—C(═O)$R^A$ is C1-C6 alkyl substituted with 3,5-dimethoxyphenyl. In some embodiments, the $R^A$ of the $R^2$—C(═O)$R^A$ is

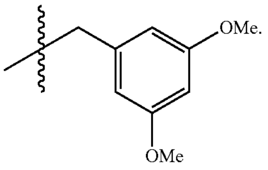 [SMILES: *Cc1cc(OC)cc(OC)c1]

In some embodiments, the $R^A$ of the $R^2$—C(═O)$R^A$ is C1-C6 alkyl substituted with unsubstituted phenyl. In some embodiments, the $R^A$ of the $R^2$—C(═O)$R^A$ is C1-C6 alkyl substituted with unsubstituted C6-C10 aryl. In some embodiments, the $R^A$ of the $R^2$—C(═O)$R^A$ is phenylmethyl. In some embodiments, the $R^A$ of the $R^2$—C(═O)$R^A$ is phenethyl. In some embodiments, the $R^A$ of the $R^2$—C(═O)$R^A$ is C1-C6 alkyl substituted with 3-9 membered heterocyclyl. In some embodiments, the $R^A$ of the $R^2$—C(═O)$R^A$ is C1-C6 alkyl substituted with methylenedioxyphenyl. In some embodiments, the $R^A$ of the $R^2$—C(═O)$R^A$ is methyl substituted with methylenedioxyphenyl. In some embodiments, the $R^A$ of the $R^2$—C(═O)$R^A$ is C1-C6 alkyl substituted with 5-methylenedioxyphenyl. In some embodiments, the $R^A$ of the $R^2$—C(═O)$R^A$ is methyl substituted with 5-methylenedioxyphenyl. In some embodiments, the $R^A$ of the $R^2$—C(═O)$R^A$ is C1-C6 alkyl substituted with —$NR^ER^F$. In some embodiments, $R^E$ and $R^F$ are each hydrogen. In some embodiments, one of $R^E$ and $R^F$ is hydrogen and the other of $R^E$ and $R^F$ is C1-C6 alkyl. In some embodiments, one of $R^E$ and $R^F$ is hydrogen and the other of $R^E$ and $R^F$ is methyl. In some embodiments, $R^E$ and $R^F$ are each independently selected C1-C6 alkyl. In some embodiments, $R^E$ and $R^F$ are each methyl. In some embodiments, the $R^A$ of the $R^2$—C(═O)$R^A$ is C1-C6 alkyl substituted with —C(═O)$OR^G$. In some embodiments, $R^G$ is hydrogen. In some embodiments, $R^G$ is C1-C6 alkyl. In some embodiments, the $R^A$ of the $R^2$—C(═O)$R^A$ is unsubstituted C1-C6 alkyl. In some embodiments, the $R^A$ C1-C6 alkyl is a C1-C4 alkyl. In some embodiments, the $R^A$ C1-C6 alkyl is methyl or ethyl. In some embodiments, the $R^A$ C1-C6 alkyl is methyl. In some embodiments, the $R^A$ C1-C6 alkyl is ethyl. In some embodiments, when the $R^A$ C1-C6 alkyl is substituted with 1-2 substituents, it is substituted with 1 substituent. In some embodiments, when the $R^A$ C1-C6 alkyl is substituted with 1-2 substituents, it is substituted with 2 substituent.

In some embodiments, the $R^A$ of the $R^4$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy; 3-9 membered heterocyclyl; —$NR^ER^F$; or —C(═O)$OR^G$. In some embodiments, the $R^A$ of the $R^4$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy;

3-9 membered heterocyclyl; $R^1$. In some embodiments, the $R^A$ of the $R^4$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy; 3-9 membered heterocyclyl. In some embodiments, the $R^A$ of the $R^4$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy. In some embodiments, the $R^A$ of the $R^4$—C(═O)$R^A$ is C1-C6 alkyl substituted with 1-2 substituents independently selected from C6-C10 aryl optionally substituted with 1-2 independently selected C1-C6 alkoxy; 3-9 membered heterocyclyl. In some embodiments, the $R^A$ of the $R^4$—C(═O)$R^A$ is C1-C6 alkyl substituted with 1-2 (e.g., 1) independently selected C3-C6 cycloalkyl. In some embodiments, the $R^A$ of the $R^4$—C(═O)$R^A$ is C1-C6 alkyl substituted with one C3-C6 cycloalkyl. In some embodiments, the $R^A$ of the $R^4$—C(═O)$R^A$ is ethyl substituted with one C3-C6 cycloalkyl. In some embodiments, the $R^A$ of the $R^4$—C(═O)$R^A$ is C1-C6 alkyl substituted with two C3-C6 cycloalkyl. In some embodiments, the $R^A$ of the $R^4$—C(═O)$R^A$ is C1-C6 alkyl substituted with cyclopropyl or cyclohexyl. In some embodiments, the $R^A$ of the $R^4$—C(═O)$R^A$ is C1-C6 alkyl substituted with one cyclohexyl. In some embodiments, the $R^A$ of the $R^4$—C(═O)$R^A$ is methyl substituted with C3-C6 cycloalkyl. In some embodiments, the $R^A$ of the $R^4$—C(═O)$R^A$ is cyclohexylmethyl. In some embodiments, the $R^A$ of the $R^4$—C(═O)$R^A$ is cyclohexylethyl. In some embodiments, the $R^A$ of the $R^4$—C(═O)$R^A$ is C1-C6 alkyl substituted with C6-C10 aryl optionally substituted with 1-2 independently selected C1-C6 alkoxy. In some embodiments, the $R^A$ of the $R^4$—C(═O)$R^A$ is C1-C6 alkyl substituted with C6-C10 aryl substituted with 1-2 independently selected C1-C6 alkoxy. In some embodiments, the $R^A$ of the $R^4$—C(═O)$R^A$ is methyl substituted with C6-C10 aryl optionally substituted with 1-2 independently selected C1-C6 alkoxy. In some embodiments, the $R^A$ of the $R^4$—C(═O)$R^A$ is C1-C6 alkyl substituted with phenyl optionally substituted with C1-C6 alkoxy. In some embodiments, the $R^A$ of the $R^4$—C(═O)$R^A$ is C1-C6 alkyl substituted with phenyl optionally substituted with 1-2 C1-C6 alkoxy. In some embodiments, the $R^A$ of the $R^4$—C(═O)$R^A$ is C1-C6 alkyl substituted with C6-C10 aryl optionally substituted with 1-2 methoxy. In some embodiments, the $R^A$ of the $R^4$—C(═O)$R^A$ is methyl substituted with C6-C10 aryl optionally substituted with 1-2 methoxy. In some embodiments, the $R^A$ of the $R^4$—C(═O)$R^A$ is C1-C6 alkyl substituted with phenyl optionally substituted with 1-2 methoxy. In some embodiments, the $R^A$ of the $R^4$—C(═O)$R^A$ is C1-C6 alkyl substituted with phenyl substituted with two methoxy. In some embodiments, the $R^A$ of the $R^4$—C(═O)$R^A$ is C1-C6 alkyl substituted with 3,5-dimethoxyphenyl. In some embodiments, the $R^A$ of the $R^4$—C(═O)$R^A$ is

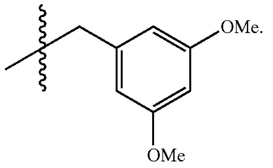 [SMILES: *Cc1cc(OC)cc(OC)c1]

In some embodiments, the $R^A$ of the $R^4$—C(═O)$R^A$ is C1-C6 alkyl substituted with unsubstituted phenyl. In some embodiments, the $R^A$ of the $R^4$—C(═O)$R^A$ is C1-C6 alkyl substituted with unsubstituted C6-C10 aryl. In some embodiments, the $R^A$ of the $R^4$, —C(═O)$R^A$ is phenylmethyl. In some embodiments, the $R^A$ of the $R^4$—C(═O)$R^A$ is phenethyl. In some embodiments, the $R^A$ of the $R^4$—C(═O)$R^A$ is C1-C6 alkyl substituted with 3-9 membered heterocyclyl. In some embodiments, the $R^A$ of the $R^4$—C(═O)$R^A$ is methyl substituted with 3-9 membered heterocyclyl. In some embodiments, the $R^A$ of the $R^4$—C(═O)$R^A$ is C1-C6 alkyl substituted with methylenedioxyphenyl. In some embodiments, the $R^A$ of the $R^4$—C(═O)$R^A$ is C1-C6 alkyl substituted with —$NR^ER^F$. In some embodiments, $R^E$ and $R^F$ are each hydrogen. In some embodiments, one of $R^E$ and $R^F$ is hydrogen and the other of $R^E$ and $R^F$ is C1-C6 alkyl. In some embodiments, one of $R^E$ and $R^F$ is hydrogen and the other of $R^E$ and $R^F$ is methyl. In some embodiments, $R^E$ and $R^F$ are each independently selected C1-C6 alkyl. In some embodiments, $R^E$ and $R^F$ are each methyl. In some embodiments, the $R^A$ of the $R^4$—C(═O)$R^A$ is C1-C6 alkyl substituted with —C(═O)$OR^G$. In some embodiments, $R^G$ is hydrogen. In some embodiments, RG is C1-C6 alkyl. In some embodiments, the $R^A$ of the $R^4$—C(═O)$R^A$ is unsubstituted C1-C6 alkyl. In some embodiments, the $R^A$ C1-C6 alkyl is a C1-C4 alkyl. In some embodiments, the $R^A$ C1-C6 alkyl is methyl or ethyl. In some embodiments, the $R^A$ C1-C6 alkyl is methyl. In some embodiments, the $R^A$ C1-C6 alkyl is ethyl. In some embodiments, when the $R^A$ C1-C6 alkyl is substituted with 1-2 substituents, it is substituted with 1 substituent. In some embodiments, when the $R^A$ C1-C6 alkyl is substituted with 1-2 substituents, it is substituted with 2 substituent.

In some embodiments, the $R^A$ of the $R^7$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy; 3-9 membered heterocyclyl; —$NR^ER^F$; or —C(═O)$OR^G$. In some embodiments, the $R^A$ of the $R^1$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy; 3-9 membered heterocyclyl; In some embodiments, the $R^A$ of the $R^1$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy; 3-9 membered heterocyclyl. In some embodiments, the $R^A$ of the $R^1$—C(═O)$R^A$ is C1-C6 alkyl substituted with 1-2 substituents independently selected from C3-C6 cycloalkyl; C6-C10 aryl optionally substituted with 1-2 independently selected C1-C6 alkoxy. In some embodiments, the $R^A$ of the $R^1$—C(═O)$R^A$ is C1-C6 alkyl substituted with 1-2 substituents independently selected from C6-C10 aryl optionally substituted with 1-2 independently selected C1-C6 alkoxy; 3-9 membered heterocyclyl. In some embodiments, the $R^A$ of the $R^7$—C(═O)$R^A$ is C1-C6 alkyl substituted with 1-2 (e.g., 1) independently selected C3-C6 cycloalkyl. In some embodiments, the $R^A$ of the $R^7$—C(═O)$R^A$ is C1-C6 alkyl substituted with one C3-C6 cycloalkyl. In some embodiments, the $R^A$ of the $R^7$—C(═O)$R^A$ is ethyl substituted with one C3-C6 cycloalkyl. In some embodiments, the $R^A$ of the $R^7$—C(═O)$R^A$ is C1-C6 alkyl substituted with two C3-C6 cycloalkyl. In some embodiments, the $R^A$ of the $R^7$—C(═O)$R^A$ is C1-C6 alkyl substituted with cyclopropyl or cyclohexyl. In some embodiments, the $R^A$ of the $R^7$—C(═O)$R^A$ is C1-C6 alkyl substituted with one cyclohexyl. In some embodiments, the $R^A$ of the $R^7$—C(═O)$R^A$ is cyclohexylethyl. In some embodiments, the $R^A$ of the $R^7$—C(═O)$R^A$ is C1-C6 alkyl substituted with C6-C10 aryl optionally substituted with 1-2 independently selected C1-C6 alkoxy. In some embodiments, the $R^A$ of the $R^7$—C(═O)$R^A$ is C1-C6 alkyl substituted with C6-C10 aryl substituted with 1-2 independently selected C1-C6 alkoxy. In some embodiments, the $R^A$ of the $R^7$—C(═O)$R^A$ is methyl substituted with C6-C10 aryl optionally substituted with 1-2 independently selected C1-C6 alkoxy. In some embodiments, the $R^A$ of the $R^7$—C(═O)$R^A$ is C1-C6 alkyl substituted with phenyl optionally substituted with C1-C6 alkoxy. In some embodiments, the $R^A$ of the $R^7$—C(═O)$R^A$ is C1-C6 alkyl substituted with phenyl optionally substituted with 1-2 C1-C6 alkoxy. In some embodiments, the $R^A$ of the $R^7$—C(═O)$R^A$ is C1-C6 alkyl substituted with C6-C10 aryl optionally substituted with 1-2 methoxy. In some embodiments, the $R^A$ of the $R^7$—C(═O)$R^A$ is methyl substituted with C6-C10 aryl optionally substituted with 1-2 methoxy. In some embodiments, the $R^A$ of the $R^7$—C(═O)$R^A$ is C1-C6 alkyl substituted with phenyl optionally substituted with 1-2 methoxy. In some embodiments, the $R^A$ of the $R^7$—C(═O)$R^A$ is C1-C6 alkyl substituted with phenyl substituted with two methoxy. In some embodiments, the $R^A$ of the $R^7$—C(═O)$R^A$ is C1-C6 alkyl substituted with 3,5-dimethoxyphenyl. In some embodiments, the $R^A$ of the $R^7$—C(═O)$R^A$ is

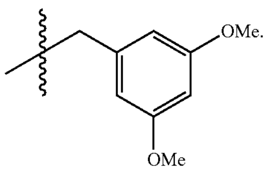 [SMILES: *Cc1cc(OC)cc(OC)c1]

In some embodiments, the $R^A$ of the $R^7$—C(═O)$R^A$ is C1-C6 alkyl substituted with unsubstituted phenyl. In some embodiments, the $R^A$ of the $R^7$—C(═O)$R^A$ is C1-C6 alkyl substituted with unsubstituted C6-C10 aryl. In some embodiments, the $R^A$ of the $R^7$—C(═O)$R^A$ is phenylmethyl. In some embodiments, the $R^A$ of the $R^7$—C(═O)$R^A$ is phenethyl. In some embodiments, the $R^A$ of the $R^7$—C(═O)$R^A$ is C1-C6 alkyl substituted with 3-9 membered heterocyclyl. In some embodiments, the $R^A$ of the $R^7$—C(═O)$R^A$ is C1-C6 alkyl substituted with methylenedioxyphenyl. In some embodiments, the $R^A$ of the $R^7$—C(═O)$R^A$ is C1-C6 alkyl substituted with —$NR^ER^F$. In some embodiments, $R^E$ and $R^F$ are each hydrogen. In some embodiments, one of $R^E$ and $R^F$ is hydrogen and the other of $R^E$ and $R^F$ is C1-C6 alkyl. In some embodiments, one of $R^E$ and $R^F$ is hydrogen and the other of $R^E$ and $R^F$ is methyl. In some embodiments, $R^E$ and $R^F$ are each independently selected C1-C6 alkyl. In some embodiments, $R^E$ and $R^F$ are each methyl. In some embodiments, the $R^A$ of the $R^7$—C(═O)$R^A$ is C1-C6 alkyl substituted with —C(═O)$OR^G$. In some embodiments, $R^G$ is hydrogen. In some embodiments, $R^G$ is C1-C6 alkyl. In some embodiments, the $R^A$ of the $R^7$—C(═O)$R^A$ is unsubstituted C1-C6 alkyl.

In some embodiments, the $R^A$ C1-C6 alkyl is a C1-C4 alkyl. In some embodiments, the $R^A$ C1-C6 alkyl is methyl or ethyl. In some embodiments, the $R^A$ C1-C6 alkyl is methyl. In some embodiments, the $R^A$ C1-C6 alkyl is ethyl. In some embodiments, when the $R^A$ C1-C6 alkyl is substituted with 1-2 substituents, it is substituted with 1 substituent. In some embodiments, when the $R^A$ C1-C6 alkyl is substituted with 1-2 substituents, it is substituted with 2 substituent.

In some embodiments, $R^1$, $R^3$, and $R^5$ are each an independently selected C1-C6 alkyl optionally substituted with C6-C10 aryl.

In some embodiments, $R^6$ is C1-C6 alkyl substituted with —$CO_2H$ or $NR^DR^E$.

In some embodiments, $R^2$, $R^4$, and $R^7$ are —C(═O)$R^A$; each occurrence of $R^A$ is an independently selected C1-C6 alkyl optionally substituted with 1-2 substituents independently selected from C3-C6 cycloalkyl; C6-C10 aryl optionally substituted with 1-2 independently selected C1-C6 alkoxy, or 3-9 membered heterocyclyl.

In some embodiments, $R^1$, $R^3$, and $R^5$ are each an independently selected C1-C6 alkyl optionally substituted with C6-C10 aryl; and $R^6$ is C1-C6 alkyl substituted with —$CO_2H$ or $NR^DR^E$.

In some embodiments, $R^1$, $R^3$, and $R^5$ are each an independently selected C1-C6 alkyl optionally substituted with C6-C10 aryl;

$R^2$, $R^4$, and $R^7$ are —C(═O)$R^A$; each occurrence of $R^A$ is an independently selected C1-C6 alkyl optionally substituted with 1-2 substituents independently selected from C3-C6 cycloalkyl; C6-C10 aryl optionally substituted with 1-2 independently selected C1-C6 alkoxy, or 3-9 membered heterocyclyl;

each occurrence of $R^D$ and $R^E$ is independently selected from hydrogen and C1-C6 alkyl.

In some embodiments, $R^6$ is C1-C6 alkyl substituted with —$CO_2H$ or $NR^DR^E$;

$R^2$, $R^4$, and $R^7$ are —C(═O)$R^A$; each occurrence of $R^A$ is an independently selected C1-C6 alkyl optionally substituted with 1-2 substituents independently selected from C3-C6 cycloalkyl; C6-C10 aryl optionally substituted with 1-2 independently selected C1-C6 alkoxy, or 3-9 membered heterocyclyl;

each occurrence of $R^D$ and $R^E$ is independently selected from hydrogen and C1-C6 alkyl.

In some embodiments, $R^1$, $R^3$, and $R^5$ are each an independently selected C1-C6 alkyl optionally substituted with C6-C10 aryl;

$R^6$ is C1-C6 alkyl substituted with —$CO_2H$ or $NR^DR^E$;

$R^2$, $R^4$, and $R^7$ are —C(═O)$R^A$; each occurrence of $R^A$ is an independently selected C1-C6 alkyl optionally substituted with 1-2 substituents independently selected from C3-C6 cycloalkyl; C6-C10 aryl optionally substituted with 1-2 independently selected C1-C6 alkoxy, or 3-9 membered heterocyclyl;

each occurrence of $R^D$ and $R^E$ is independently selected from hydrogen and C1-C6 alkyl.

In some embodiments, the compound is M-2-5:

M-2-5

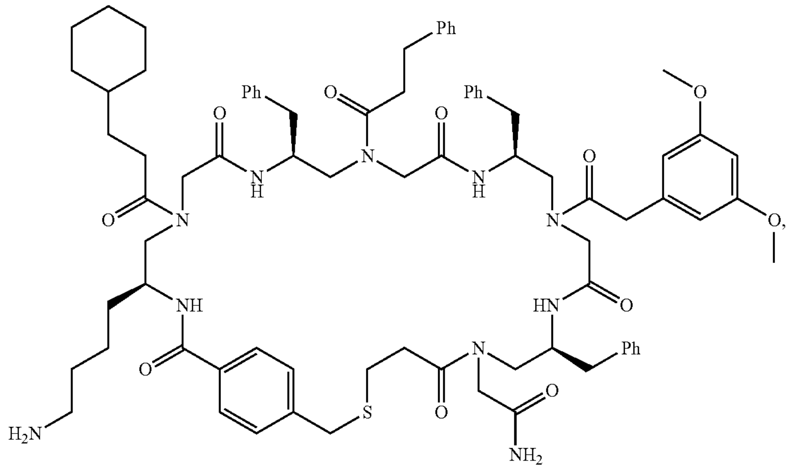

or a pharmaceutically acceptable salt thereof.

Pharmaceutical Compositions

The compounds disclosed herein may be incorporated into pharmaceutical compositions suitable for administration to a subject (such as a human or non-human subject). For example, disclosed herein is a pharmaceutical composition comprising a compound of Formula (I), or a pharmaceutically acceptable salt thereof, and at least one pharmaceutically acceptable excipient.

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the disclosure are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of the present disclosure, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The terms "pharmaceutically acceptable carrier" and "pharmaceutically acceptable excipient," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In some embodiments, the chemical entities described herein or a pharmaceutical composition thereof can be administered to subject in need thereof by any accepted route of administration. Acceptable routes of administration include, but are not limited to, oral, parenteral, transdermal, intranasal, sublingual, neuraxial, or ocular.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry,* 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Methods of Treatment

Disclosed herein is a method of treating cancer in a subject in need thereof, comprising administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method of treating an EGFR-associated cancer in a subject in need thereof, comprising administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method for treating cancer in a subject in need thereof, comprising:

(a) determining if the cancer is associated with a dysregulation of an EGFR receptor, or expression or activity or level of any of the same; and (b) if the cancer is determined to be associated with a dysregulation of an EGFR receptor, or expression or activity or level of any of the same, administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method for treating an EGFR-associated cancer in a subject in need thereof, comprising:

(a) determining if the cancer is associated with a dysregulation of an EGFR receptor, or expression or activity or level of any of the same; and (b) if the cancer is determined to be associated with a dysregulation of an EGFR receptor, or expression or activity or level of any of the same, administering to the subject an effective amount of a compound of Formula (I) or a pharmaceutically acceptable salt thereof, or a pharmaceutical composition comprising a compound of Formula (I) or a pharmaceutically acceptable salt thereof, to a subject having a clinical record that indicates that the subject has a dysregulation of an EGFR receptor, or expression or activity or level of any of the same.

Disclosed herein is a method of treating a subject, the method comprising administering a therapeutically effective amount of a compound of Formula (I) or a pharmaceutically acceptable salt thereof, or a pharmaceutical composition comprising a compound of Formula (I) or a pharmaceutically acceptable salt thereof.

In some embodiments, the step of determining that the cancer in the subject is associated with a dysregulation of an EGFR receptor, or expression or activity or level of any of the same includes performing an assay to detect dysregulation in a EGFR gene, a EGFR protein, or expression or activity or level of any of the same in a sample from the subject. In some embodiments, the EGFR receptor is in the extracellular domain.

In some embodiments, the method further comprises obtaining a sample from the subject. In some embodiments, the sample is a biopsy sample.

In some embodiments, the assay is a Western blot.

Disclosed herein is a method for inhibiting metastasis in a subject having cancer in need of such treatment, comprising administering to the subject an effective amount of a compound of Formula (I) or a pharmaceutically acceptable salt thereof, or a pharmaceutical composition comprising a compound of Formula (I) or a pharmaceutically acceptable salt thereof.

Disclosed herein is a method for inhibiting tumorigenesis in a subject having cancer in need of such treatment, comprising administering to the subject an effective amount of a compound of Formula (I) or a pharmaceutically acceptable salt thereof, or a pharmaceutical composition comprising a compound of Formula (I) or a pharmaceutically acceptable salt thereof.

In some embodiments, the cancer is selected from glioma, lung cancer, head cancer, neck cancer, breast cancer, prostate cancer, pancreatic cancer, and colon cancer.

In some embodiments, the method further comprises administering an additional therapy or therapeutic agent to the subject. In some embodiments, the additional therapy or therapeutic agent is selected from radiotherapy, cytotoxic chemotherapeutics, kinase targeted-therapeutics, apoptosis modulators, signal transduction inhibitors, immune-targeted therapies, monoclonal antibodies, and angiogenesis-targeted therapies. In some embodiments, the additional therapeutic agent is selected from erlotinib, gefitinib, afatinib, erlotinib, brigatinib, icotinib, panitumumab, zalutumumab, nimotuzumab, matuzumab, lapatinib, osimertinib, fulvestrant, capecitabine, trastuzumab, ado-trastuzumab emtansine, pertuzumab, paclitaxel, nab-paclitaxel, enzalutamide, olaparib, pegylated liposomal doxorubicin (PLD), trametinib, ribociclib, palbociclib, buparlisib, AEB071, everolimus, exemestane, cisplatin, letrozole, AMG 479, LSZ102, LEE011, cetuximab, AUY922, BGJ398, MEK162, LJM716, LGH447, imatinib, gemcitabine, LGX818, amcenestrant, and combinations thereof. In some embodiments, the additional therapeutic agent is selected from the group consisting of a glucagon-like peptide-1 (GLP-1) receptor agonist, a sodium-glucose transport protein 2 (SGLT-2) inhibitor, a dipeptidyl peptidase 4 (DPP-4) inhibitor, metformin, and combinations thereof.

In some embodiments, the compound of Formula (I) or a pharmaceutically acceptable salt thereof, or a pharmaceutical composition comprising a compound of Formula (I) or a pharmaceutically acceptable salt thereof, and the additional therapeutic agent are administered simultaneously as separate dosages.

In some embodiments, the compound of Formula (I) or a pharmaceutically acceptable salt thereof, or a pharmaceutical composition comprising a compound of Formula (I) or a pharmaceutically acceptable salt thereof, and the additional therapeutic agent are administered as separate dosages sequentially in any order.

Disclosed herein is a method for inhibiting mammalian cell proliferation, comprising contacting the mammalian cell with a compound of Formula (I) or a pharmaceutically acceptable salt thereof.

Disclosed herein is a method for inhibiting EGFR receptor activity in a mammalian cell, comprising contacting the mammalian cell with a compound of Formula (I) or a pharmaceutically acceptable salt thereof. In some embodiments, inhibiting EGFR receptor activity comprises interacting the compound of Formula (I) or a pharmaceutically acceptable salt thereof, with EGFR glutamine residue Q384, Q411, or both. In some embodiments, inhibiting EGFR receptor activity comprises interacting the compound of Formula (I) or a pharmaceutically acceptable salt thereof, with EGFR glutamine side chain Q384. In some embodiments, inhibiting EGFR receptor activity comprises interacting the compound of Formula (I), with EGFR glutamine side chain Q411. In some embodiments, inhibiting EGFR receptor activity comprises inhibiting EGFR phosphorylation. In some embodiments, inhibiting EGFR phosphorylation comprises downregulating EGFR receptor activity. In some embodiments, inhibiting EGFR phosphorylation comprises inhibiting downstream activation of phosphorylation of AKT, ERK, or both. In some embodiments, inhibiting EGFR receptor activity comprises inhibiting tyrosine kinase activation. In some embodiments, the compound further inhibits AKT and/or ERK phosphorylation. In some embodiments, inhibiting EGFR receptor activity comprises reducing the binding constant $K_a$ (i.e., association constant) of each of one or more endogenous EGFR ligands. In some embodiments, each of the one or more endogenous EGFR ligands is selected from the group consisting of: epidermal growth factor (EGF), transforming growth factor-α (TGF-α), β-cellulin (BTC), heparin-binding EGF-like growth factor (HB-EGF), amphiregulin (AREG), epiregulin (EREG), and epigen (EPI). In some embodiments, the endogenous EGFR ligand is epidermal growth factor (EGF). In some embodiments, the compound binds to EGFR with a $K_D$ of less than about 5 μM (e.g., less than about 5 μM, less than about 4 μM, less than about 3 μM, less than about 2 μM, less than about 1 μM, less than about 700 nM, less than about 400 nM, less than about 200 nM, less than about 100 nM, about 100 nM, about 200 nM, about 300 nM, about 400 nM, about 430 nM, about 500 nM, about 600 nM, about 700 nM, about 800 nM, about 900 nM, or about 1 μM).

Disclosed herein is a method for inhibiting EGFR phosphorylation in a mammalian cell, comprising contacting the mammalian cell with a compound of Formula (I) or a pharmaceutically acceptable salt thereof. In some embodiments, the phosphorylation is tyrosine phosphorylation. In some embodiments, the phosphorylation is EGF-stimulated tyrosine phosphorylation. In some embodiments, the phosphorylation is autophosphorylation. In some embodiments, the compound inhibits stimulation of EGFR phosphorylation by an endogenous EGFR ligand (e.g., EGF) with an $IC_{50}$ of 150 μM or lesser (e.g., 130 μM or lesser, 100 μM or lesser, 80 μM or lesser, 60 μM or lesser, 40 μM or lesser, 30 μM or lesser, 20 μM or lesser, 10 μM or lesser, 1 μM or lesser, 500 nM or lesser, 400 μM or lesser, 300 μM or lesser, 200 μM or lesser, 100 μM or lesser, 50 μM or lesser, 10 μM or lesser, 5 μM or lesser, 1 μM or lesser, 10 μM, 11 μM, 15 μM, 17 μM, 18 μM, 20 μM, 25 μM, or 30 μM. In some embodiments, the compound inhibits stimulation of AKT phosphorylation with an $IC_{50}$ of 150 μM or lesser (e.g., 130 μM or lesser, 100 μM or lesser, 80 μM or lesser, 60 μM or lesser, 40 μM or lesser, 30 μM or lesser, 20 μM or lesser, 10 μM or lesser, 1 μM or lesser, 500 nM or lesser, 400 μM or lesser, 300 μM or lesser, 200 μM or lesser, 100 μM or lesser, 50 μM or lesser, 10 μM or lesser, 5 μM or lesser, 1 μM or lesser, 10 μM, 11 μM, 15 μM, 17 μM, 18 μM, 20 μM, 25 μM, or 30 μM. In some embodiments, the compound inhibits stimulation of ERK phosphorylation with an $IC_{50}$ of 150 μM or lesser (e.g., 130 μM or lesser, 100 μM or lesser, 80 μM or lesser, 60 μM or lesser, 40 μM or lesser, 30 μM or lesser, 20 μM or lesser, 10 μM or lesser, 1 μM or lesser, 500 nM or lesser, 400 μM or lesser, 300 μM or lesser, 200 μM or lesser, 100 μM or lesser, 50 μM or lesser, 10 μM or lesser, 5 μM or lesser, 1 μM or lesser, 10 μM, 11 μM, 15 μM, 17 μM, 18 μM, 20 μM, 25 μM, or 30 μM.

In some embodiments, the contacting occurs in vivo. In some embodiments, the contacting occurs in vitro. In some embodiments, the mammalian cell is a mammalian cancer cell. In some embodiments, the mammalian cancer cell is a mammalian EGFR-associated cancer cell. In some embodiments, the mammalian cancer cell is an A549 cell. In some embodiments, the cell has a dysregulation of an EGFR gene, a EGFR protein, or expression or activity or level of any of the same. In some embodiments, the compound is at least 1-fold selective toward cancer cells over normal cells, e.g., at least 2-fold, at least 3-fold, at least 4-fold, at least 5-fold, at least 6-fold, at least 7-fold, at least 8-fold, at least 9-fold, at least 10-fold, or about 8-fold selective toward cancer cells over normal cells.

In some embodiments, the subject exhibits decreased migration of cancer cells. In some embodiments, the decreased migration of cancer cells is demonstrated by, for example, a scratch wound assay that shows a lower degree of healing than a negative control at least 10 hours after application of the compound.

In some embodiments, less than 5% (e.g., less than 4%, less than 3%, less than 2%, less than 1%, or less than 0.5%) of the compound of Formula (I) decomposes when exposed to ammonium bicarbonate buffer at 37° C. for 20 h. In some embodiments, no decomposition of the compound of Formula (I) is detected when exposed to ammonium bicarbonate buffer at 37° C. for 20 h.

In some embodiments, the compound has an apparent permeability value of at least $20\times10^{-6}$ cm/s (e.g., at least $30\times10^{-6}$ cm/s, at least $40\times10^{-6}$ cm/s, at least $50\times10^{-6}$ cm/s, at least $60\times10^{-6}$ cm/s, at least $65\times10^{-6}$ cm/s, at least $70\times10^{-6}$ cm/s, at least $75\times10^{-6}$ cm/s, at least $80\times10^{-6}$ cm/s, at least $85\times10^{-6}$ cm/s, at least $90\times10^{-6}$ cm/s, at least $100\times10^{-6}$ cm/s, at least $120\times10^{-6}$ cm/s, at least $140\times10^{-6}$ cm/s, at least $160\times10^{-6}$ cm/s, at least $180\times10^{-6}$ cm/s, at least $200\times10^{-6}$ cm/s, about $60\times10^{-6}$ cm/s, about $65\times10^{-6}$ cm/s, about $70\times10^{-6}$ cm/s, about $75\times10^{-6}$ cm/s, about $80\times10^{-6}$ cm/s, about $85\times10^{-6}$ cm/s, or about $90\times10^{-6}$ cm/s) in a parallel artificial membrane permeability assay—blood brain barrier (PAMPA-BBB) assay.

Kits

The compounds disclosed herein may be included in kits comprising the compound, a systemic or topical composition, or both; and information, instructions, or both that use of the kit will provide treatment for medical conditions in mammals (particularly humans). The kit may include an additional pharmaceutical composition for use in combination therapy. The kit may include buffers, reagents, or other components to facilitate the mode of administration. The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

EXAMPLES

Library Synthesis and Screening.

The OBTC combinatorial library was synthesized as reported previously on solid phase synthesis. In the library, each TentaGel bead was spatially segregated in two layers, which incorporated a cyclic γ-AApeptide on the surface layer and a unique linear α-peptides tag on the inner layer. The cyclic γ-AApeptide was constructed through combinatorial synthesis using five γ-AApeptides building blocks and eight side chains, and the cyclization was achieved through the formation of the thioether bridge by sulfur-mediated $S_N2$ reaction (FIG. 1A). As a result, the OBTC combinatorial library was expected to have a theoretical diversity of 320,000 compounds which were displayed in triple. In addition, the linear peptides tag consisted of seven α-amino acid residues which are uniquely related to every cyclic γ-AApeptide on the same bead.

The quality of the library was first assessed. The MALDI-TOF MS/MS analysis of ten randomly selected beads showed that nine beads have unambiguous MS/MS fragmentation patterns, suggesting the quality of the beads is excellent. Subsequently, the high-throughput screening for the extracellular domain of EGFR protein was directly performed with the library. Briefly, the OBTC library was firstly incubated with Fc-Tagged recombinant EGFR protein, followed by incubation with Goat anti-human IgG Fc cross adsorbed secondary antibody, Dylight 549. After a thorough wash, beads emitting intensive red fluorescence (FIG. 2) were isolated from the library under a fluorescence microscope. The brightly red bead is the positive bead which was picked up manually. These beads were treated with guanidium chloride (GdmCl) to denature any binding proteins and then the linear encoding peptides in the inner layers of the beads were cleaved off by treatment with CNBr and subsequently sequenced by tandem MS/MS of MALDI. The structures of five putative hits were determined unambiguously.

Cyclic peptides M-2-5 Binds to EGFR and Inhibits EGFR, AKT, ERK phosphorylation In Vitro.

Figure 3:
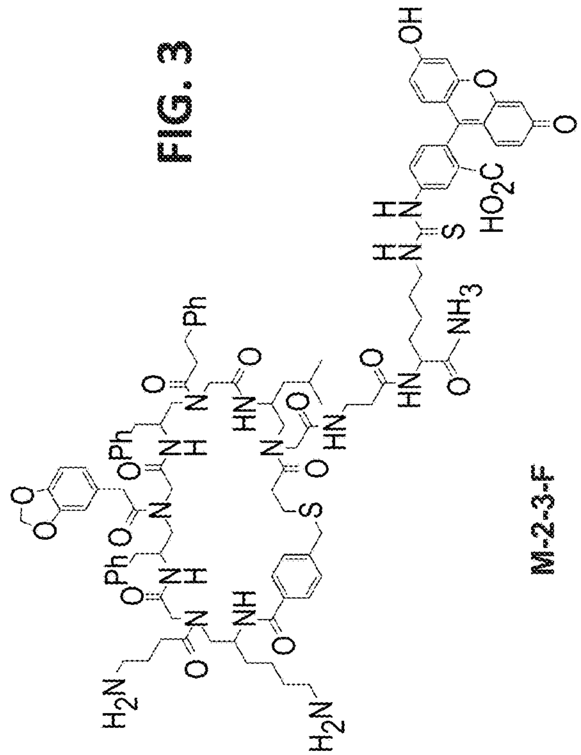
FIG. 3 shows chemical structures of fluorescein isothiocyanate-labeled cyclic γ-AApeptides.
Figure 3:
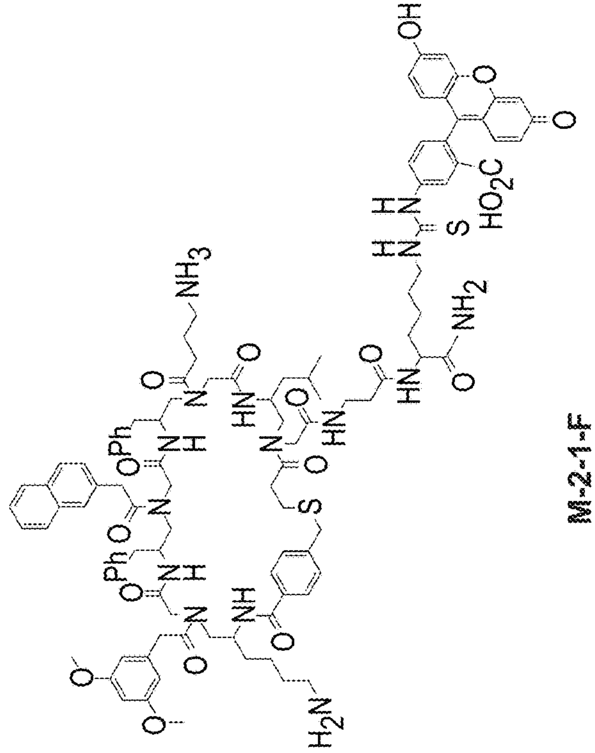
Figure 3:
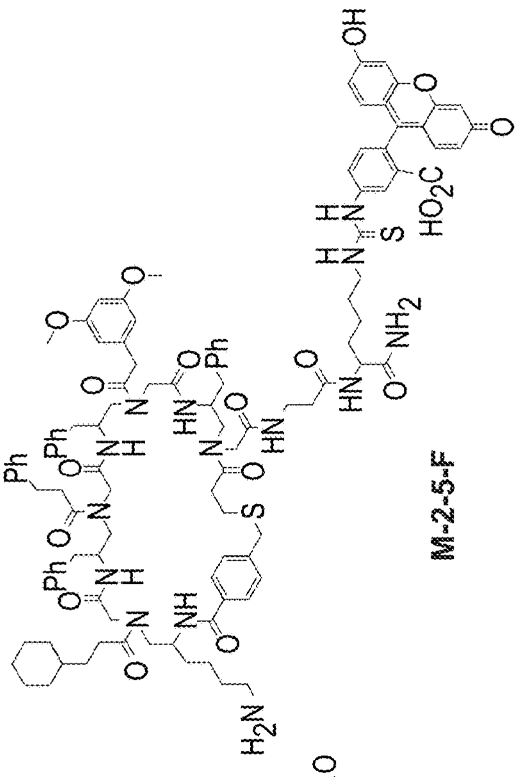
Figure 3:
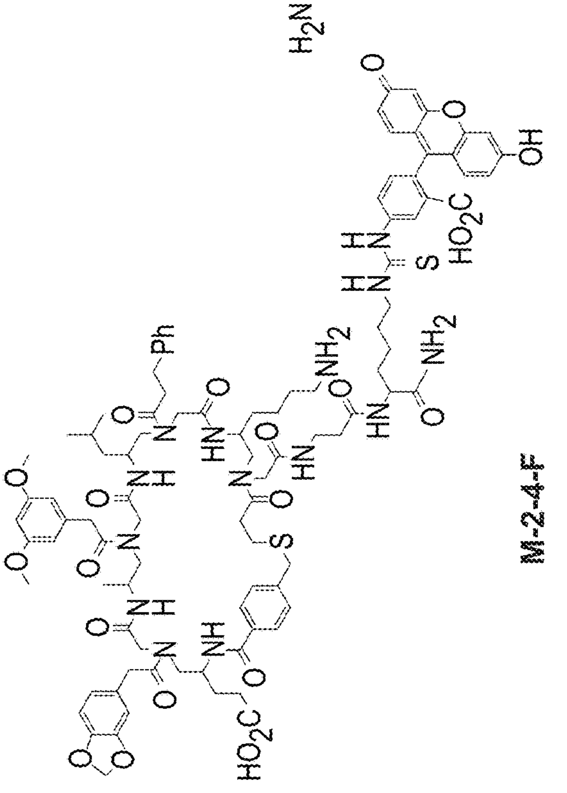
Figure 4A:
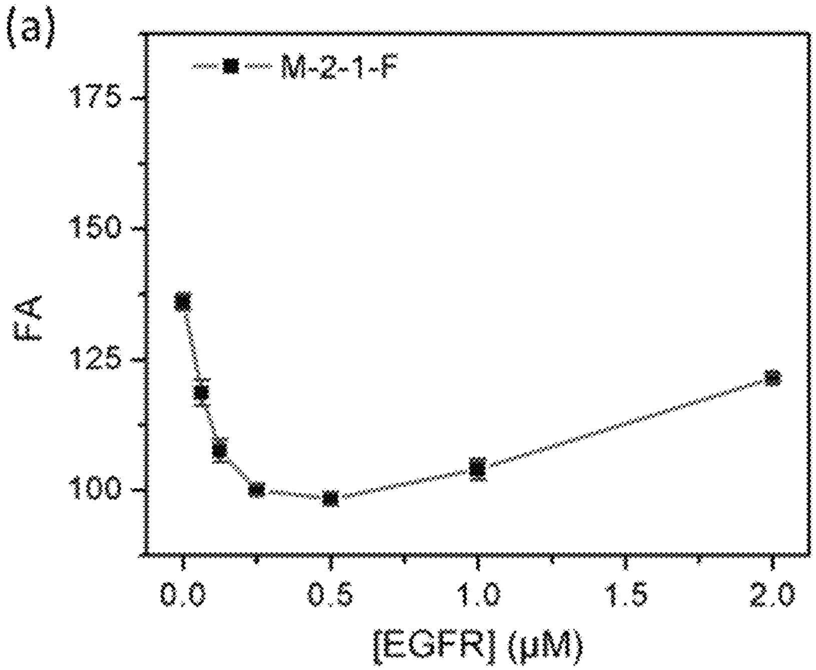
FIG. 4A is a plot of the binding affinity of M-2-1-F to EGFR measured by a fluorescence polarization (FP) assay.
Figure 4B:
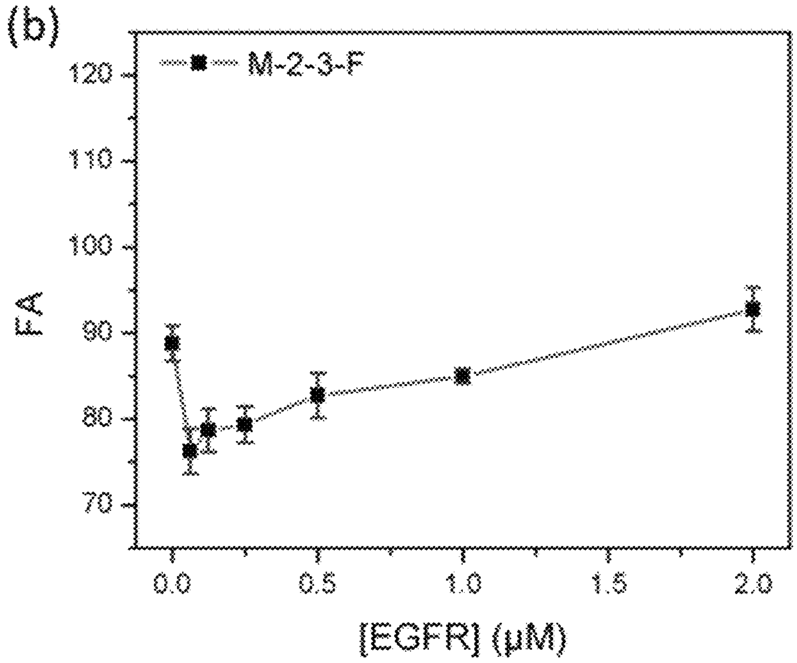
FIG. 4B is a plot of the binding affinity of M-2-3-F to EGFR measured by a fluorescence polarization (FP) assay.
Figure 4C:
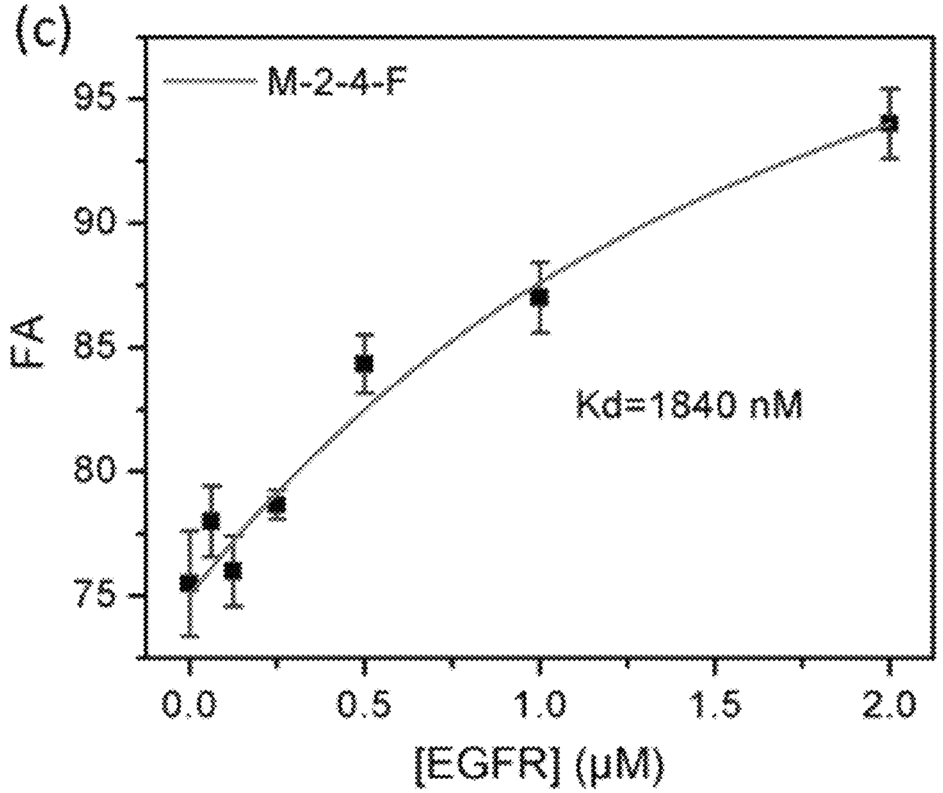
FIG. 4C is a plot of the binding affinity of M-2-4-F to EGFR measured by a fluorescence polarization (FP) assay.

It was first determined whether the identified hits could bind to EGFR in vitro. To this end, fluorescein isothiocyanate (FITC) labeled hits whose structures were confirmed by MALDI-TOF MS/MS (FIG. 3) were resynthesized on a larger scale individually and tested for their binding affinity toward the extracellular domain of EGFR using a fluorescence polarization (FP) assay. Among them, M-2-5-F bound to EGFR with a $K_D$ of 0.43 μM (FIG. 1B), and the others show quite weak binding to EGFR (FIGS. 4A-4C).

Figure 5A:
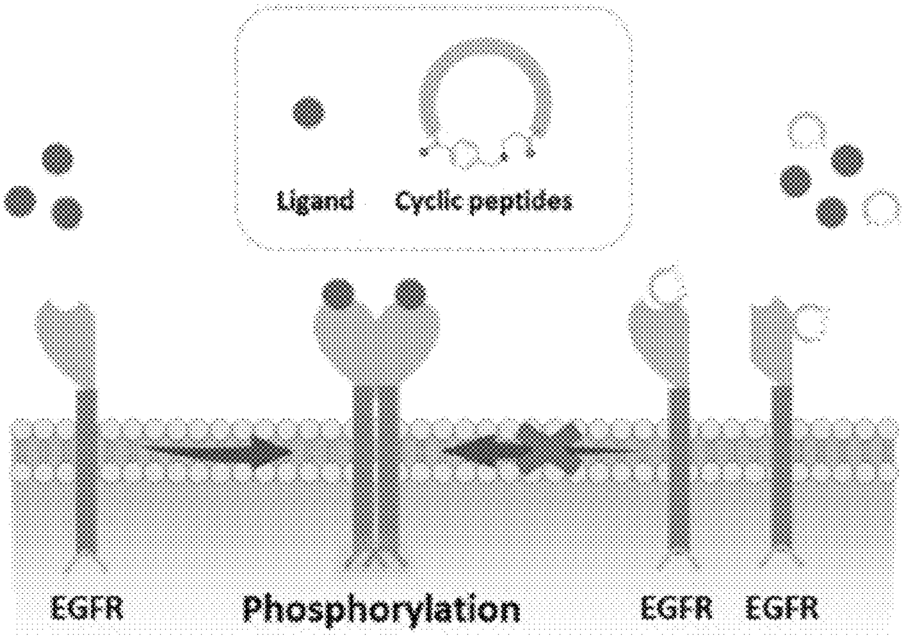
FIG. 5A is an illustration of the proposed mechanism of how cyclic peptides inhibit EGFR phosphorylation.
Figure 5B:
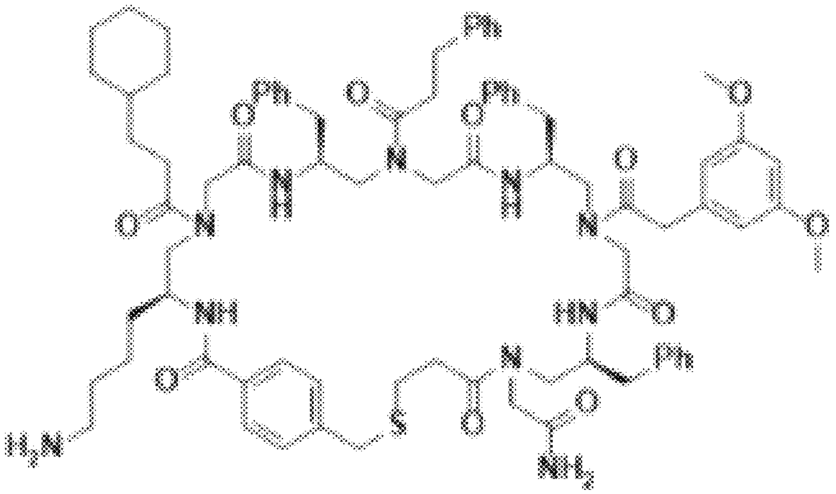
FIG. 5B is the chemical structure of M-2-5.

Having confirmed the binding activity in vitro, the activity of M-2-5 (FIG. 5B) was tested at the cellular level. It is recognized that the extracellular domain of EGFR contains four subdomains, two of which are used for ligand binding and one of which is involved in homodimerization and heterodimerization. The EGFR ligand family comprises seven transmembrane precursor proteins, including epidermal growth factor (EGF), transforming growth factor-α (TGF-α), β-cellulin (BTC), heparin-binding EGF-like growth factor (HB-EGF), amphiregulin (AREG), epiregulin (EREG), and epigen (EPI). The cyclic AApeptides, which may bind to any sits on the extracellular domain of EGFR, and therefore may compete with natural ligands for EGF/EGFR binding, result in inhibition of the EGFR mediated signaling pathway such as tyrosine kinase activation (FIG. 5A).

Figure 5C:
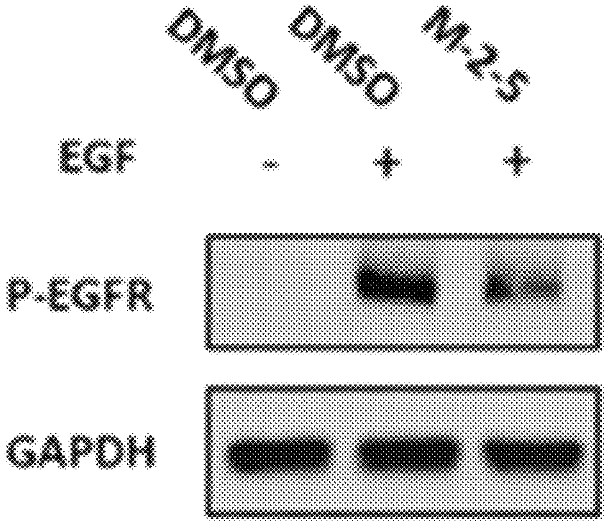
FIG. 5C is a western blot analysis showing the effect of 20 μM M-2-5 on EGF-induced EGFR phosphorylation using GAPDH as an internal control. Data are representative of three independent experiments.
Figure 5D:
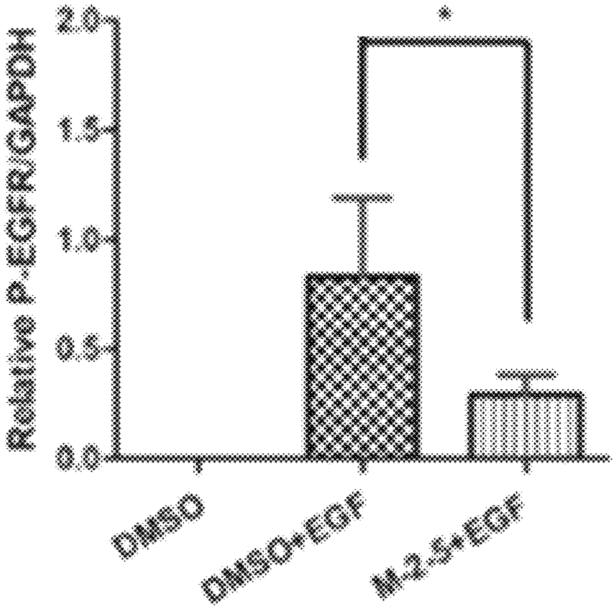
FIG. 5D is a plot of the expression ratio of relative P-EGFR/GAPDH. *$P<0.05$ vs. EGF-stimulation.
Figure 5E:
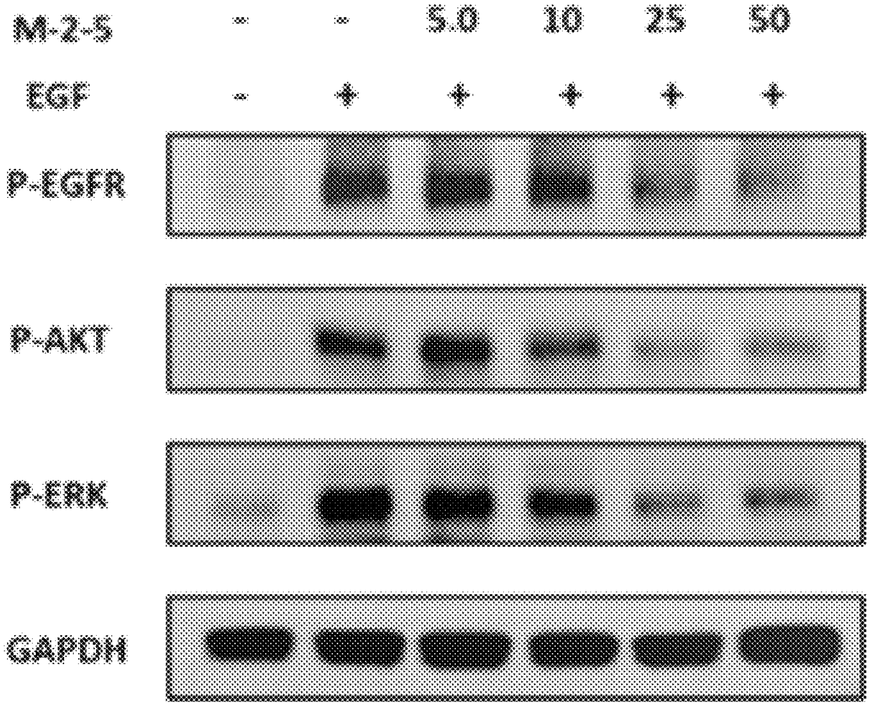
FIG. 5E is a western blot of cell lysates of starved A549 cells pretreated with M-2-5 (0 to 50 μM) for 4 h before stimulation with EGF (100 ng/ml) for 5 min with antibodies against the indicated proteins. Data are representative of three independent experiments.
Figure 5F:
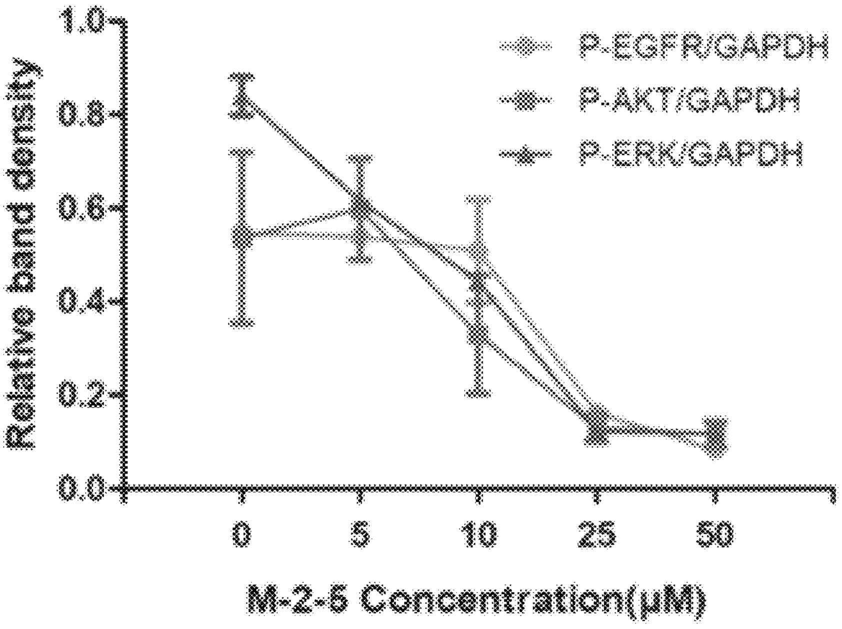
FIG. 5F is a plot of the relative band density of P-EGFR/GAPDH, P-AKT/GAPDH and P-ERK/GAPDH vs. M-2-5 concentration, where the intensity of each strip was analyzed by ImageJ software.

In order to determine the effect of M-2-5 on the phosphorylation level of EGFR (P-EGFR), starved A549 cells were pretreated with M-2-5 for 4 h before further stimulation with 100 ng/mL of the natural ligand EGF, and cell lysates were analyzed by western blotting. A549 cells were chosen due to their elevated expression of EGFR. As shown in FIG. 5C, stimulation of cells with EGF led to significant tyrosine phosphorylation of EGFR. Intriguingly, M-2-5 blocked a vast majority of EGFR activation (FIGS. 5C and 5D) which indicated M-2-5 is a potent inhibitor of EGFR. The ability of M-2-5 to inhibit EGF-stimulated tyrosine phosphorylation of EGFR, as well as downstream AKT and ERK pathways in a dose-dependent manner was then investigated. As shown in FIG. 5E, pretreatment of starved A549 cells with M-2-5 (0-50 μM) for 4 h resulted in a concentration-dependent inhibition of EGF stimulation of EGFR phosphorylation with an $IC_{50}$ of 17.7 μM and an almost complete blockage at 25 μM or more. Furthermore, downstream activation of phosphorylation of both AKT and ERK were also inhibited by M-2-5 in vitro with the consistent potency ($IC_{50}$ for AKT is 8.75 μM; and $IC_{50}$ for ERK is 11.2 μM) in a dose-dependent manner (FIGS. 5E and 5F). Together, these data indicated that M-2-5 is a potent inhibitor of EGFR and its downstream signaling pathways.

M-2-5 Inhibits Cancer Cell Proliferation and Migration In Vitro.

Figure 5G:
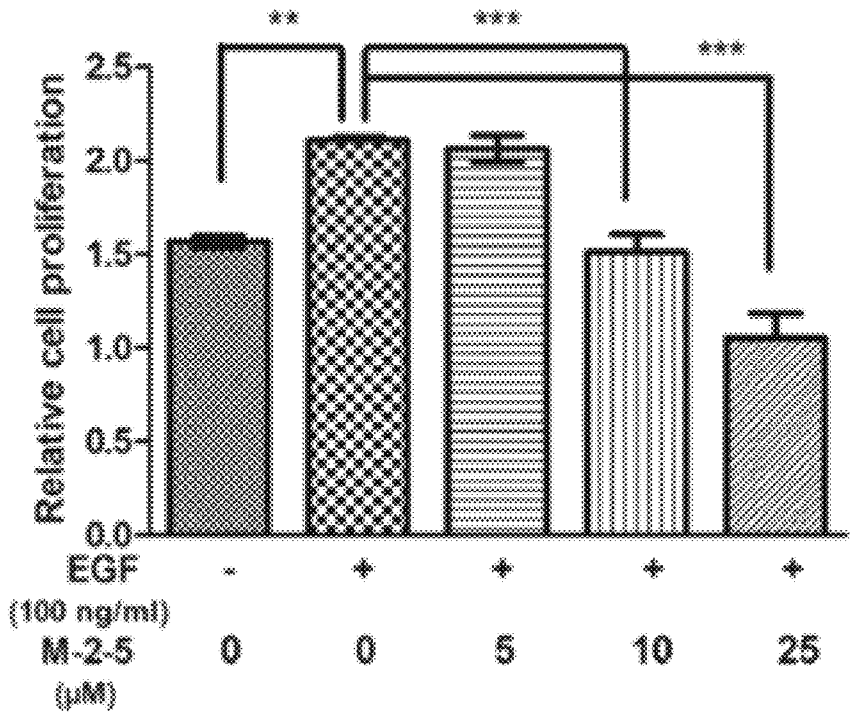
FIG. 5G is a bar graph showing the effect of M-2-5 on cell proliferation inhibition in vitro. A549 cells were treated with increasing concentrations of M-2-5 in the present of EGF for 48 h, and cell viability was determined using CCK-8 kits. Means were derived from four replicates (n=4). $P<0.05$ vs. EGF-stimulation, *$P<0.001$ vs. EGF-stimulation.

As cell proliferation is an important aspect of tumorigenesis, cell proliferation assay was carried out to further analyze the effect of M-2-5 on EGF-driven proliferation of A549 cells in vitro. A549 cells were treated with serum-reduced EGF-containing (100 ng/mL) DMEM in the presence of M-2-5 at different concentration (0-25 μM) for 48 h. As shown in FIG. 5G, A549 cells show significantly enhanced proliferation upon the stimulation of EGF, in contrast, a significantly antiproliferative activity of M-2-5 on EGF-stimulated cells was observed in a dose-dependent manner with an $IC_{50}$ of 8.23 μM (FIG. 5G), and a complete suppression of cell proliferation at ~10 compared to the control group that without EGF stimulation. M-2-5 exhibited excellent selectivity toward cancer cells over normal cells (~8 fold), as its $IC_{50}$ for Human Embryonic Kidney HEK293 cells was found to be 62.1 μM.

Figures 6A, 6B, 6C, 6D:
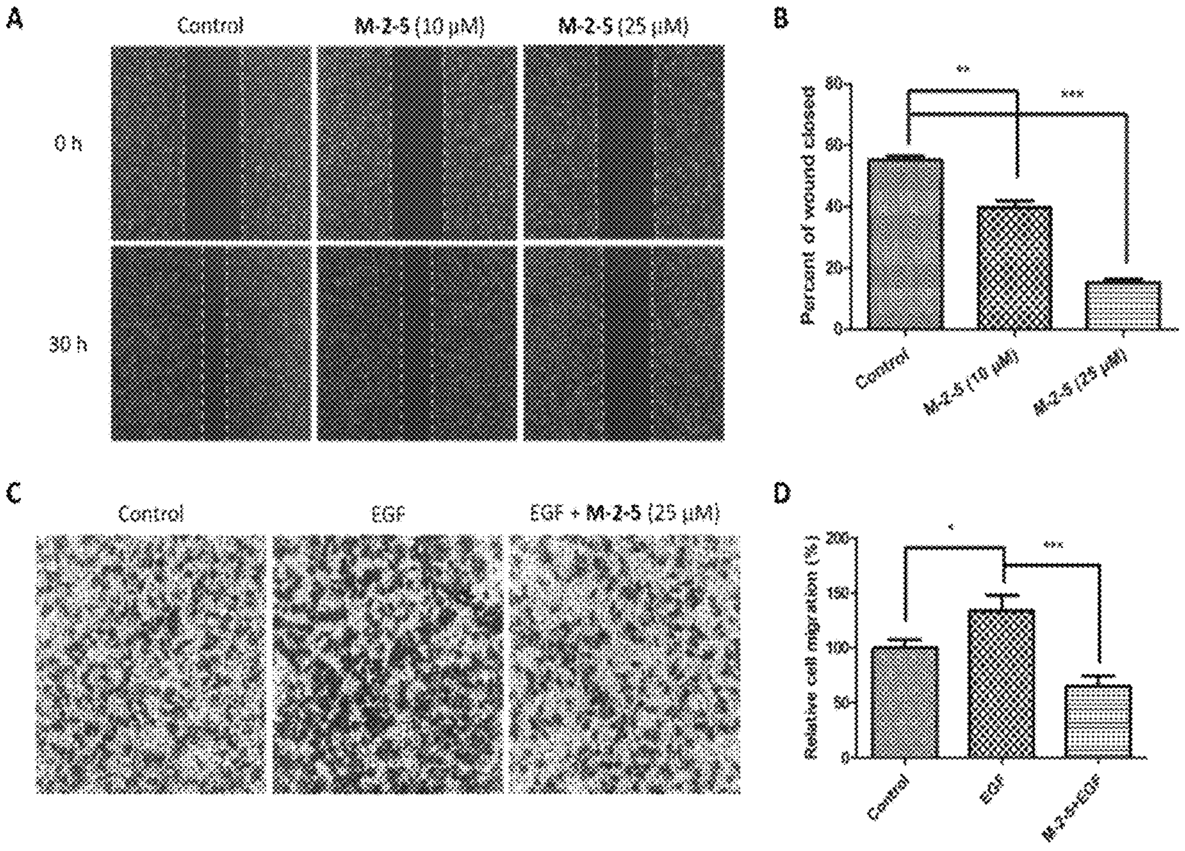
FIG. 6A depicts images of wound healing assay on A549 cells showing a negative control, and the assay in the presence of M-2-5 (10 and 25 The experiments were repeated three times with similar results, and images of one representative experiment taken at 0 and 30 h after wound scratching are shown. A549 cells were photographed at 4× magnification.
FIG. 6B is a bar graph depicting the percentage of wound healing covered at 30 h. $P<0.01$ compared with control at 30 h; *$P<0.001$ compared with control at 30 h.
FIG. 6C depicts images of a transwell assay migration assay of A549 cells upon treatment of EGF alone or EGF+M-2-5 (25 The A549 cells without EGF and M-2-5 treatment were used as control. After stained with crystal violet, A549 cells were photographed at 20× magnification.
FIG. 6D is a bar graph depicting quantitative results of migration assays. The columns represent the mean of cell numbers from at least three independent experiments. The relative cell migration counted manually and the number of migration cells in the control group was set to 100%. *$P<0.05$ compared with control at 12 h, ***$P<0.001$ compared with EGF-stimulation at 12 h.

M-2-5's inhibitory effect on cell migration of A549 cells, which plays an important role in tumor metastatic activity, was then investigated. First, a scratch-wound assay was established to investigate the cell migratory behaviors. As expected, the percent of wound closed was notably decreased upon treatment with 25 μM M-2-5 (15.2%) for 30 h, leading to 40% decrease compared with untreated control A549 cells (55.3%) (FIGS. 6A and 6B). Similar suppression in migration ability was also observed in transwell assay, as shown in FIG. 6C. Compared with the untreated control group, the number of migrating cells were distinctly increased to 133.9% in the presence of EGF (FIG. 6D), which were dramatically decreased to 64.8% with M-2-5 (25 μM) treatment. Taken together, M-2-5 has been shown to significantly inhibit A549 cells proliferation and migration ability.

Stability of M-2-5 Toward Enzymatic Hydrolysis.

Figure 7A:
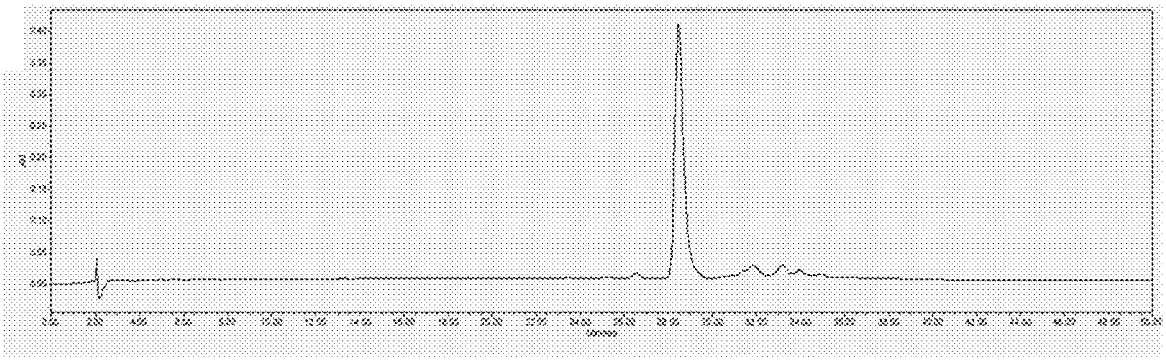
FIG. 7A is an HPLC trace of M-2-5 before incubation with pronase (0.1 mg/mL) in 100 mM ammonium bicarbonate buffer at 37° C. for 20 h.
Figure 7B:
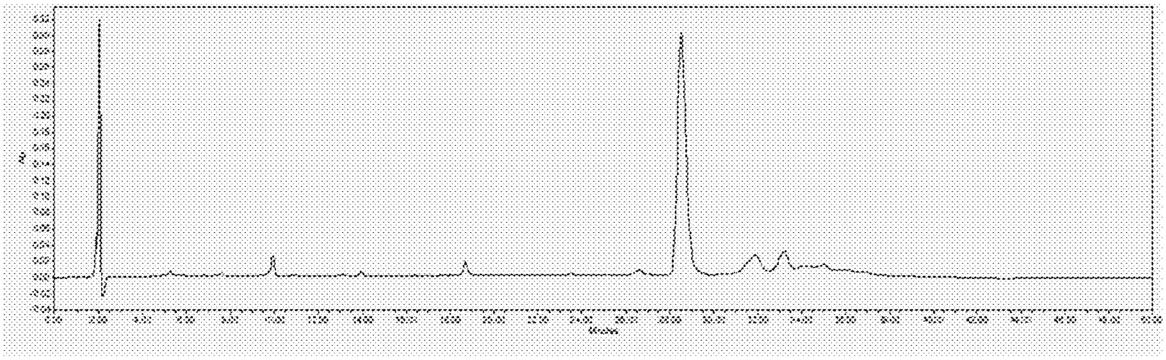
FIG. 7B is an HPLC trace of M-2-5 after incubation with pronase (0.1 mg/mL) in 100 mM ammonium bicarbonate buffer at 37° C. for 20 h.

As M-2-5 is a promising ligand to block EGFR signaling in vitro, its enzymatic stability toward pronase (the enzyme theoretically digesting peptides into single amino acids), which is critical for their potential biological activity in vivo was evaluated. Upon Incubation with pronase in 100 mM ammonium bicarbonate buffer at 37° C. for 20 h, no detectable degradation was observed for M-2-5 monitored by HPLC (FIG. 7), demonstrating its extraordinary stability against proteolytic degradation.

Parallel Artificial Membrane Permeability Assays (PAMPA) of M-2-5

Figure 8A:
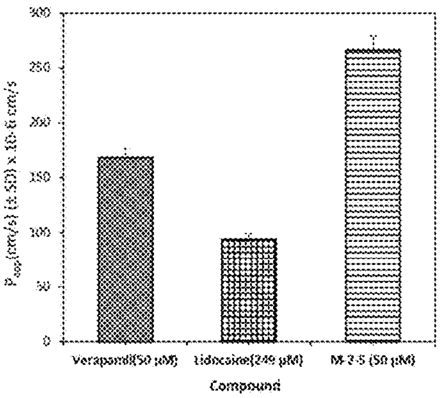
FIG. 8A is a bar graph showing results of a PAMPA-BBB assay on standards and M-2-5 at pH 7.4.
Figure 8B:
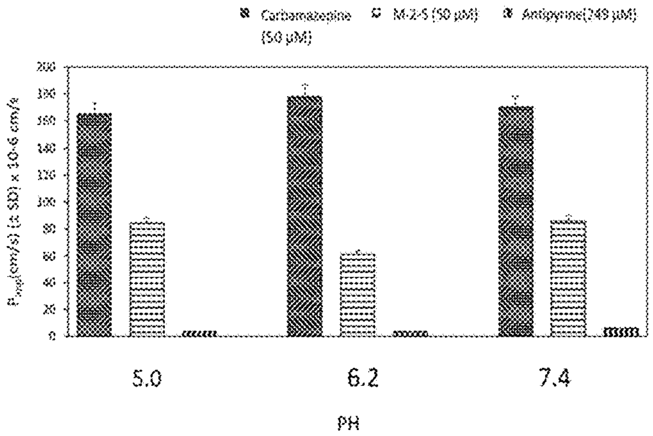
FIG. 8B is a bar graph showing results of a PAMPA-GIT assay on standards and M-2-5 at different pH conditions.

The parallel artificial membrane permeability assay (PAMPA) has been widely used in the pharmaceutical industry as a high throughput permeability assay to evaluate drug candidates.[31] As such, both the Blood-brain barrier (BBB) parallel artificial membrane permeability assay (PAMPA-BBB) and the gastro-intestinal tract (GIT) parallel artificial membrane permeability assay (PAMPA-GIT) were conducted to further evaluate the potential of M-2-5 as a drug candidate. The PAMPA-BBB is used to predict the ability of a drug for crossing the BBB.[32] The PAMPA-GIT is used for the evaluation of how the oral drug candidate might be absorbed across the entire GIT. In the PAMPA-BBB assay, Verapamil and Lidocaine were used as the positive and negative control compounds, Verapamil can easily cross the BBB, exhibiting a very high apparent permeability ($P_{app}$) value in permeability assay ($P_{app}>20\times10^{-6}$ cm/s), whereas Lidocaine could hardly pass through the BBB. As shown in FIG. 8A, Verapamil in the concentration of 50 exhibited a favorable $P_{app}$ ($(169\pm4)\times10^{-6}$ cm/s), and Lidocaine displayed a lower $P_{app}$ value ($(94\pm3)\times10^{-6}$ cm/s) even with a quite high concentration. Surprisingly, M-2-5 showed a fabulous high $P_{app}$ value of 266 ($\pm6$)$\times10^{-6}$ cm/s even in the concentration of 50 μM. The result demonstrated that M-2-5 possesses the promising potential to be further investigated as a novel drug candidate. For the PAMPA-GIT assay, it is significant to test different pH conditions since human intraluminal pH is different in stomach, duodenum, ileum, caecum, and rectum. Carbamazepine and Antipyrine were used as the positive and negative control compounds for the assay. Carbamazepine, a fully orally bioavailable compound with >90% absorption in the human gastrointestinal tract, however, Antipyrine is a poorly orally bioavailable compound that exhibits low $P_{app}$ values. As shown in FIG. 8B, M-2-5 exhibited favorable $P_{app}$ without pH-dependence. The findings indicated the M-2-5 has the potential of oral bioavailability for future drug development.

Short-Term Therapy of M-2-5 In Vivo.

Figure 10:
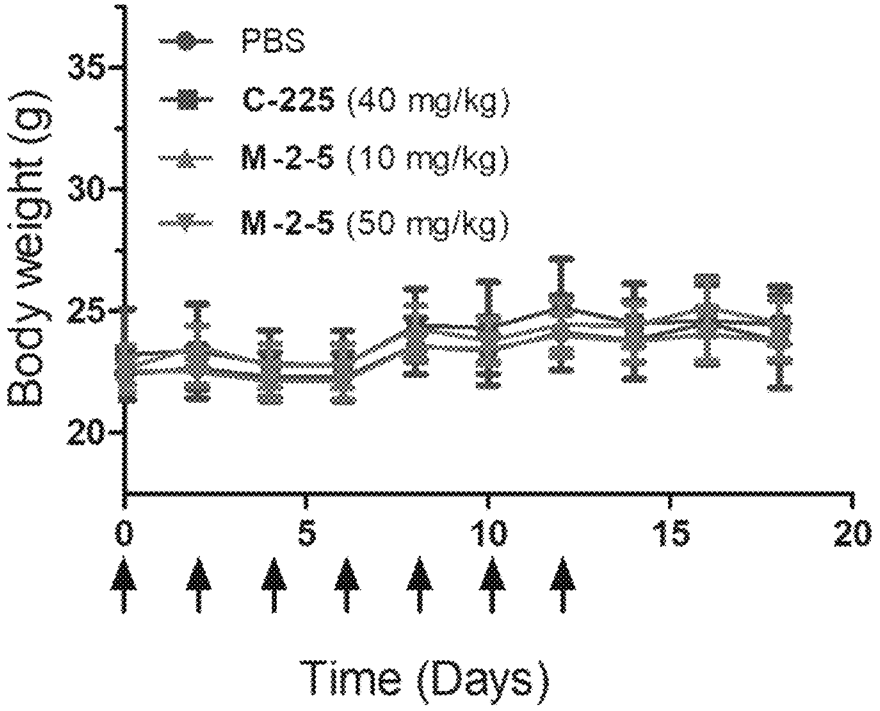
FIG. 10 depicts a mice body weight shift curve of the mice during the experiment. Arrows indicate the time of compounds treatment.

Based upon the observed strong inhibition of cell proliferation and migration, the ability to inhibit EGFR cell signaling pathways in vitro, as well as the remarkable stability against proteolytic degradation, the antitumor activity of M-2-5 in a A549 lung tumor xenograft mouse model was evaluated in vivo. PBS was used as a negative control while C225 (cetuximab), a monoclonal antibody was used as a positive control, which has been approved by FDA for treating lung, head and neck cancer. Mice were intraperitoneally administered with PBS, C225 (40 mg/kg) and M-2-5 (10 mg/kg, 50 mg/kg), respectively every two days for seven times. After another 6 days post injection, mice were sacrificed, and tumors were resected. As shown in FIG. 9A, a significant reduction in tumor volume was observed between the PBS group and the group receiving C225 therapy. Though no significant differences were found for 10 mg/kg of M-2-5 treatment, the injection of M-2-5 in high concentration (50 mg/kg) demonstrated significant suppression of tumor growth. In addition, injection of the compound did not affect the body weight gain of A549 tumor xenografted mice (FIG. 10). To confirm the expression level of P-EGFR and downstream signaling, the total proteins were extracted from tumor tissues in each group and subjected to immunoblotting of P-EGFR, P-ARK and P-ERK. Western blot analysis (FIG. 9B) show that either C225 or M-2-5 (50 mg/kg) cause dramatic decrease in P-EGFR and P-AKT, whereas M-2-5 (50 mg/kg) treatment exhibited slightly weaker efficiency in the inhibition of P-ERK compared to C225, which may account for the difference on inhibition of tumor growth. In addition, the phosphorylation level of EGFR in the A549 tumor sections was analyzed by immunohistochemical staining. As shown in FIG. 9C, consistent to western blot analysis, the staining intensity of P-EGFR, P-AKT and P-ERK were decreased respectively compared with PBS group. Taken together, these data show that M-2-5 exhibits similar anti-tumor effectiveness compared to cetuximab in A549 xenografted model. Compared to cetuximab, M-2-5 has much smaller molecular weight and therefore low production cost. Together with its similar function to monoclonal antibody and its high resistance toward proteolytic degradation, it could be further investigated for promising clinical anti-cancer drug development.

Molecular Docking Study

Figure 11:
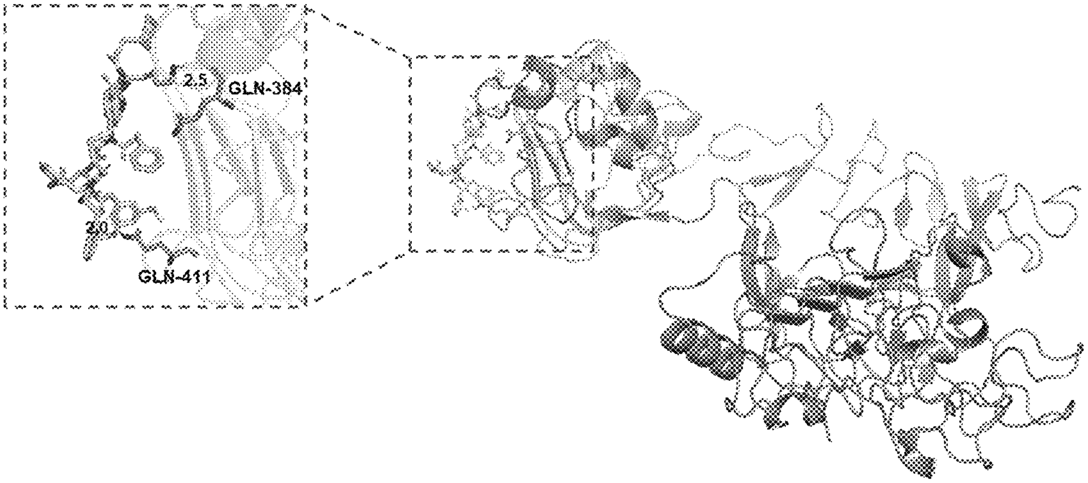
FIG. 11 shows molecular docking of M-2-5 with EGFR extracellular domain (PDB: 1YY9). The docking was performed using the Glide module in Schrödinger (2015) with default parameters, and the docking results were visualized in Pymol.

As M-2-5 could directly target the extracellular domain of EGFR and show comparable in vivo efficacy, its binding mode may be analogous to that of cetuximab. As such, molecular docking study was carried out to gain insight into the binding of M-2-5 toward EGFR. As shown in FIG. 11, the docking of M-2-5 with the extracellular domain of EGFR (PDB: 1YY9) suggested that M-2-5 could occupy the cetuximab binding site of EGFR. It was observed that an amino group and a carbonyl group of M-2-5 respectively oriented to form hydrogen bonds with two glutamine side chains from EGFR (Q384 and Q411). It is noticed that Q384 is also the key residue for the interaction between EGFR and cetuximab. The docking results strongly supported the potential of M-2-5 as novel artificial antibody targeting EGFR.

In conclusion, the foregoing study identified, e.g., a novel cyclic γ-AApeptide M-2-5 which could inhibit EGFR phosphorylation through an OBTC combinatorial library screening. The results implicated that M-2-5 could interfere with EGFR-EGF binding, resulting in inhibition of EGFR phosphorylation and downstream signal transduction, as well as suppression of cell proliferation and migration. In addition, unlike regular peptides, M-2-5 is completely resistant to proteolytic degradation. More importantly, M-2-5 also demonstrated robust antitumor activity in tumor xenografts. Compared with known small molecular inhibitors of EGFR, which are mainly tyrosine kinase inhibitors (TKIs), M-2-5 has a few advantages. First, unlike those tyrosine kinase inhibitors which targeting kinase site in the intracellular domain of EGFR, M-2-5 targets the extracellular domain of EGFR, and therefore it doesn't have to have good cell permeability. Meanwhile, it is known that tyrosine kinase inhibitors (TKIs) lack good selectivity as the kinase sites are highly conserved; this is why generally TKIs exhibit high toxicity and frequently lead to drug resistance. In contrast, M-2-5 show excellent selectivity between cancer cells and normal cells. The ability of M-2-5 to mimic monoclonal antibody, as well as its small molecular weight and high stability, could enable it a promising candidate for the development of novel anti-cancer therapeutics. The result also suggested that the approach of OBTC γ-AApeptides library provides an effective strategy for discovering human cancer therapies.

Experimental Section

Materials

All chemicals were purchased from commercial suppliers and used without further purification. Fmoc-protected amino acids were purchased from Chem-impex. TentaGel resin (0.23 mmol/g) was purchased from RAPP Polymere. Rink Amide-MBHA resin (0.55 mmol/g) was purchased from GL Biochem. Solid phase synthesis was conducted in peptide synthesis vessels on a Burrell Wrist-Action shaker. Cyclic γ-AApeptides were analyzed and purified on a Waters Breeze 2 HPLC system, and then lyophilized on a Labcono lyophilizer. The purity of the compounds was determined to be >95% by analytical HPLC. Masses of γ-AApeptides and the MS/MS analysis were obtained on an Applied Biosystems 4700 Proteomics Analyzer.

The A549 cell line was kindly provided by Prof. Lixin Wan at the Moffitt Cancer Center, Tampa, USA. EGF was purchased from Fisher Scientific; EGFR was purchased from Creative BioMart; Anti-phospho-EGFR antibody was purchased from Life Technologies; Anti-phospho-AKT and Anti-phospho-ERK antibodies were from Cell Signaling Technology; GAPDH Loading control monoclonal antibody was purchased from Invitrogen. PAMPA assays were performed on a TECAN Fredom EVO150 robot and analyzed by the pION's PAMPA Evolution Software.

One-Bead-Two-Compound Library Synthesis, Screening and Analysis

The one-bead-two-compound library was synthesized according to the scheme below. 6.26 g TentaGel $NH_2$ resin was used for the library synthesis. The building blocks, side chains, linkers and Dde-protected amino acids that were used in this library are shown below.

Scheme 1
The preparation of cyclic γ-AApeptides library.
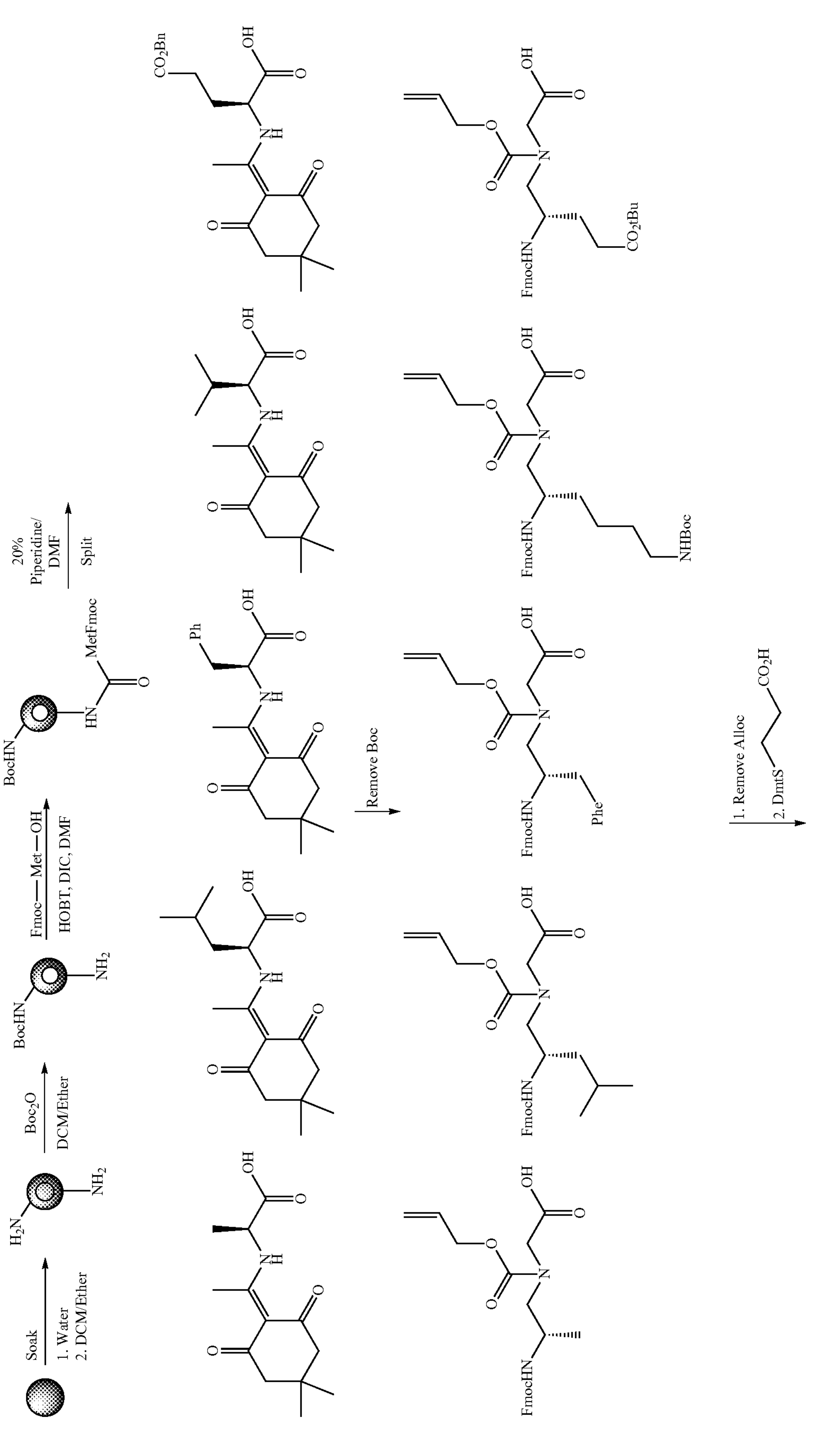

-continued
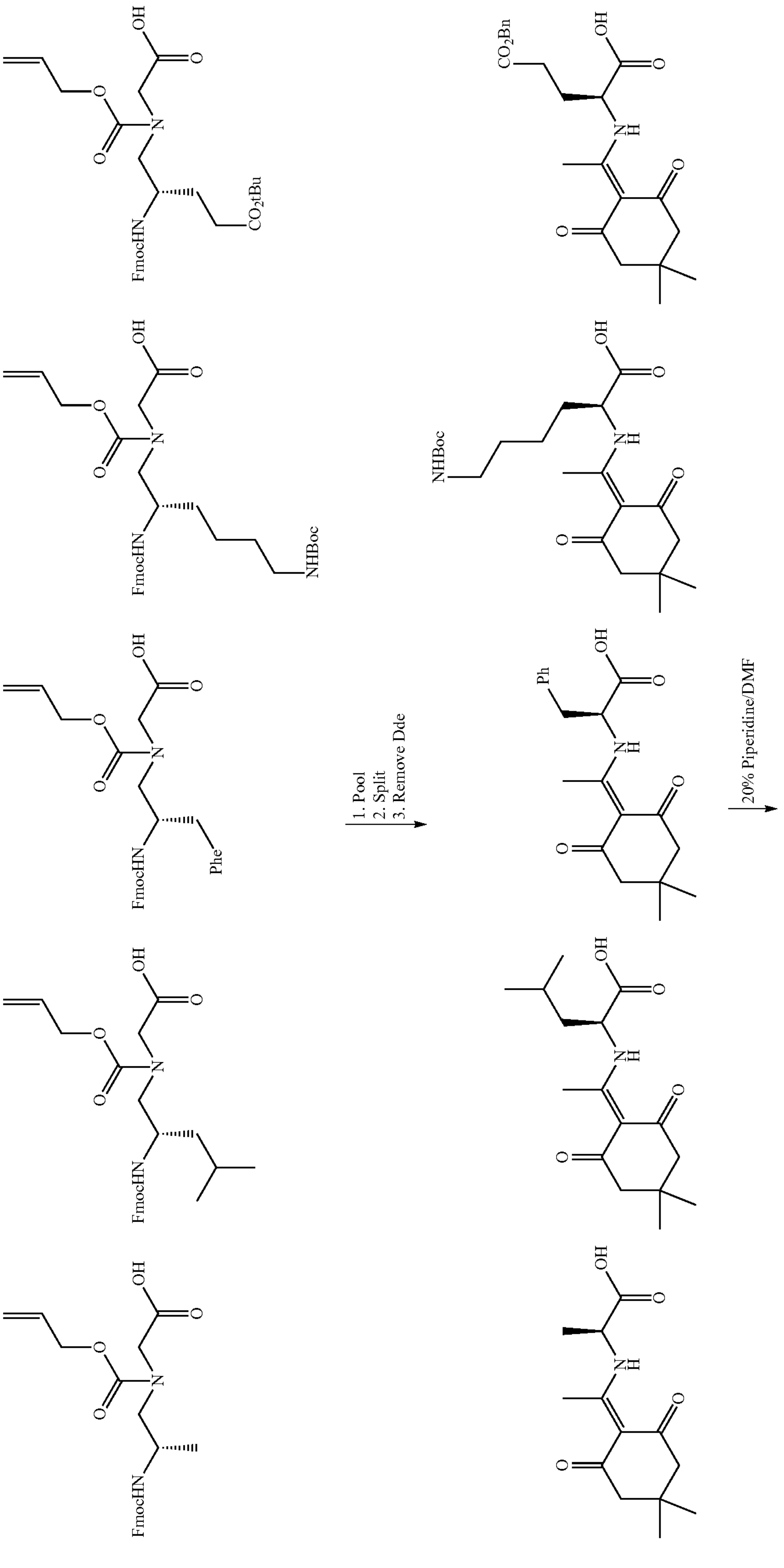

-continued
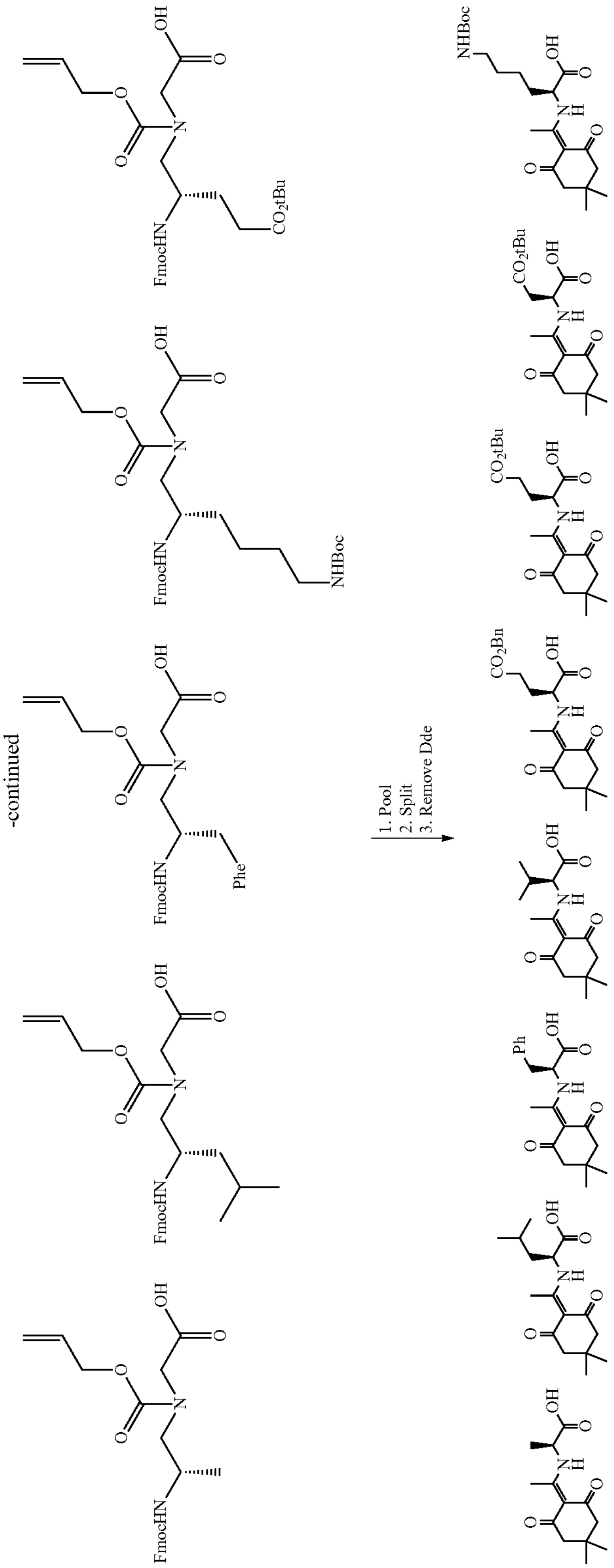

-continued
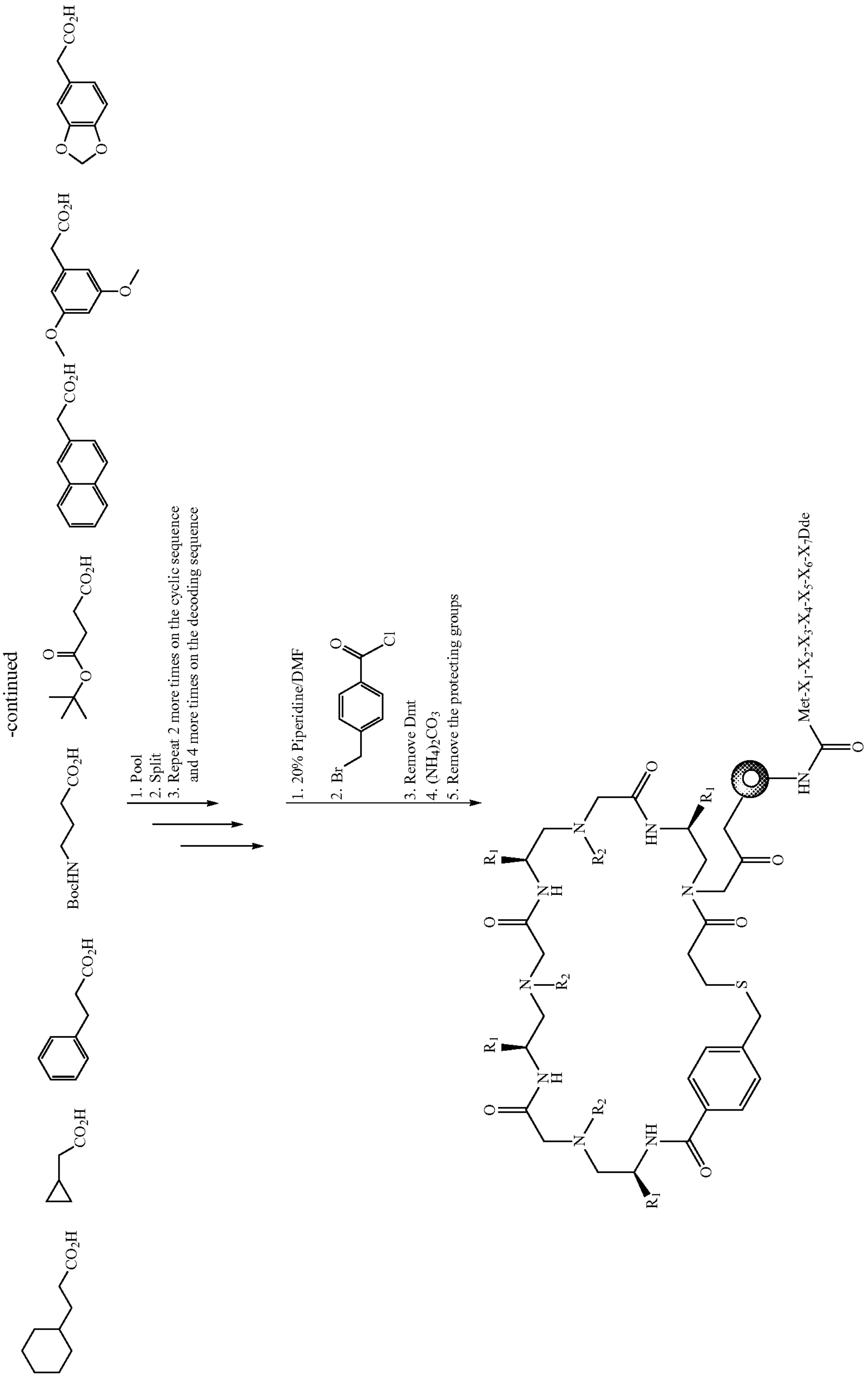

For the EGFR targeted library screening, it contains two main parts, prescreening and screening. Firstly, for the prescreening, all the TentaGel beads were swelled in DMF for 1 h. After being washed with Tris buffer for five times, the beads were equilibrated in Tris buffer overnight at room temperature, followed by incubation with the blocking buffer (1% BSA in Tris buffer with a 1000× excess of cleared *E. coli* lysate) for 1 h. After a thorough wash with Tris buffer, the beads were incubated with Goat anti-human IgG Fc cross adsorbed secondary antibody, Dylight 549 (1:1000 dilution) for 2 h at room temperature. The beads were washed with the Tris buffer for five times and then the beads emitting red fluorescence were picked up manually and excluded from formal screening.

Secondly, for the screening, the rest of beads after prescreening were washed with Tris buffer, and treated with 8 M guandine·HCl at room temperature, after 1 h, the beads were washed by DI water (5×), tris buffer (5×) and DMF (5×). The beads were then incubated in DMF for 1 h, followed by washing and equilibration in Tris buffer overnight. The beads were incubated in 1% BSA/Tris buffer and 1000× excess of *E. coli* lysate for 1 h at room temperature. After wash with Tris buffer for five times, the beads were incubated with EGFR protein at a concentration of 50 nM for 4 h at room temperature with a 1000× excess of *E. coli* lysate. After the thorough wash with Tris buffer, the library beads were incubated with and Goat anti-human IgG Fc cross adsorbed secondary antibody, Dylight 549 (1:1000 dilution) for 2 h at room temperature. The beads were washed with the Tris buffer for five times and then the beads emitting red fluorescence were picked up for future analysis.

For the hit structure analysis, each hit was transferred to an Eppendorf microtube, and denatured in 100 μM guanidine·HCl for 1 h at room temperature respectively. The bead was rinsed with Tris buffer 3×10 min, water 3×10 min, DMF 3×10 min, and ACN 3×10 min. At last the resin was placed in ACN overnight in each microtube and then ACN was evaporated. The bead was incubated in the cocktail of 5:4:1 (v:v:v) of ACN:glacial acetic acid:$H_2O$ containing cyanogen bromide (CNBr) at a concentration of 50 mg/mL overnight at room temperature. The cleavage solution was then evaporated, and the cleaved peptide was dissolved in ACN:$H_2O$ (4:1) and subject to MALDI-TOF for MS/MS analysis.

Synthesis of Cyclic γ-AApeptides

The FITC-labeled hits were re-synthesized on the Rink Amide resin[25,26]. Briefly, the Fmoc-Lys (Dde)-OH was first attached to the Rink amide resin. The Fmoc protection group was then removed, followed by the desired building blocks needed for the sequence synthesis. After the γ-AApeptides were cyclized, the Dde group was removed and Fmoc-β-Ala was added, the Fmoc protection group was then removed and FITC (2 equiv.) and DIPEA (6 equiv.) in DMF were added to the resin and shaken for 12 h at room temperature. The FITC labeled cyclic γ-AApeptides was cleaved by 1:1 (v/v) DCM/TFA containing 2% triisopropylsilane. The crude was purified by the Waters HPLC system.

M-2-1-F: MS: calcd. For $C_{105}H_{125}N_{16}NaO_{18}S_2^+$ [(M+Na)$^+$]: 1870.8661. MALDI-TOF found: m/z 1971.2394.

M-2-3-F: MS: calcd. For $C_{101}H_{122}N_{15}O_{18}S_2^+$ [(M+H)$^+$]: 1896.8528. MALDI-TOF found: m/z 1897.3221.

M-2-4-F: MS: calcd. For $C_{109}H_{120}N_{14}NaO_{22}S_2^+$ [(M+Na)$^+$]: 2063.8035. MALDI-TOF found: m/z 2064.2830.

M-2-5-F: MS: calcd. For $C_{110}H_{130}N_{14}NaO_{18}S_2^+$ [(M+Na)$^+$]: 2023.4392. MALDI-TOF found: m/z 2023.5481.

The synthesis of M-2-5 was conducted on the Rink Amide resin with general solid phrase synthesis. After the γ-AApeptides were cyclized, the compounds were cleaved by 1:1 (v/v) DCM/TFA containing 2% triisopropylsilane and purified by the Waters HPLC system.

M-2-5: MS: calcd. For $C_{80}H_{102}N_{10}NaO_{11}S^+$ [(M+Na)$^+$]: 1434.8042. MALDI-TOF found: m/z 1434.1172.

Fluorescence Polarization Assay.

The FP experiment was performed by incubating 50 nM FITC labeled AApeptides with EGFR (0 to 2 μM) in PBS. Dissociation constants (Kd) was determined by plotting the fluorescence anisotropy values as a function of protein concentration, and the plots were fitted to the following equation. The Lst is the concentration of the AApeptides and the x stands for the concentration of the protein. The experiments were conducted in triplicates and repeated for three times.

$$y=FPmin+(FPmax-FPmin)*(KD+Lst+x-sqrt((KD+Lst+x)^2-4*Lst*x))/(2*Lst)$$

Enzymatic Stability Assay.

Cyclic γ-AApeptides M-2-5 (0.1 mg/mL) were incubated with 0.1 mg/mL protease in 100 mM ammonium bicarbonate buffer (pH 7.8) at 37° C. for 20 h. Then, the reaction mixtures were concentrated in a speed vacuum to remove water and ammonium bicarbonate. The resulting residues were re-dissolved in $H_2O$/MeCN and analyzed on a Waters analytical HPLC system.

Cell Cultures and Inhibition of EGF-Induced Cell Proliferation.

A549 cells were cultured in high-glucose DMEM (Gibco) medium containing 10% fetal bovine serum and 1% penicillin/streptomycin in an atmosphere of 5% $CO_2$ at 37° C. A549 cells in good condition were seeded into a 96-well plate at a concentration of $1\times10^3$ cells/well in 100 of complete growth medium. After 24 hours of attachment at 37° C. and 5% $CO_2$, medium was replaced by fresh serum reduced DMEM and cell were serum-starved overnight. And then serum-reduced EGF (100 ng/mL) DMEM in the present of different concentration of M-2-5 was added to the cells in hexa-duplicate. After 48 h, the CCK-8 reagents were added according to the manufacturer's recommendations. The cytotoxicity of M-2-5 toward HEK293 cells was conducted in a similar fashion except no EGF was used to stimulate the cell growth.

Western Blot Assay.

A549 cells were seeded into a 6-well plate at a concentration of $1\times10^5$ cells/well. After 12 h attachment at 37° C. and 5% $CO_2$, the cells were starved overnight in serum-reduced DMEM followed by treatment with different concentration of M-2-5 for 4 h. The cells were further stimulated with 100 ng/mL of EGF for 10 min, washed with ice-cold PBS and resuspended in ice-cold RIPA buffer supplemented with Halt Protease and Phosphatase Inhibitor Cocktail. Subsequently, the cells were incubated on ice for 10 min and centrifuged at 14,000×g at 4° C. for 10 min. An equal amount of protein was run on 4~12% Bis-Tris gels, transferred to polyvinylidene difluoride membranes (Millipore) and western blotted with anti-phosphorylated EGFR, anti-phosphorylated AKT, anti-phosphorylated ERK and GAPDH. The experiments were conducted in triplicates and repeated for three times.

Cell Wound Healing Assay.

A549 cells in good condition were seeded into a 12-well plate at a concentration of $5\times10^4$ cells/well. After 24 h attachment at 37° C. and 5% $CO_2$, they reached confluence as a monolayer. The monolayer was scratched gently and slowly with a new 200 μL pipette tip across the center of the well straightly. After scratching, the well was washed twice with medium to remove the detached cells. The well was then replenished with fresh medium containing different concentration of M-2-5. The photo was taken for the scratched monolayer and then captured again after 30 h for the same wound. The wound width was measured by ImageJ. The experiments were conducted in triplicates and repeated for three times.

Transwell Assay.

A549 cells in good condition were seeded into a 100 mm dish at a concentration of $5\times10^5$ cells. After overnight attachment at 37° C. and 5% $CO_2$, culture medium was replaced with serum reduced DMEM medium, and the dish was returned to incubator for 24 h. Cells were the detached and resuspended in DMEM at a concentration of $1\times10^6$ cells/mL. Next, 100 μL of cell solution was plated on top of the filter membrane in a transwell insert and incubated for 10 minutes at 37° C. and 5% $CO_2$ to allow the cells to settle down. Subsequently, 600 μL of the desired chemo-attractant was added very carefully into the bottom of the lower chamber in a 24-well plate. The culture was incubated for 12 h, and then the transwell insert was removed from the plate. A cotton-tipped applicator was used as many times as needed to carefully swab the inside of each insert. Cells were fixed by 70% ethanol, stained by 0.2% crystal violet and visualized by microscope. Transwell data was determined by the number of the migrated cells and the value from parental cells was arbitrarily set at 100%. The experiments were conducted in triplicates and repeated for three times.

PAMPA-BBB Assay.

The parallel artificial membrane permeability assay—blood brain barrier (PAMPA-BBB) assay procedure was realized by using a method developed by pION. All liquid handling steps for the PAMPA assay are performed on a TECAN Fredom EVO150 robot and analyzed by the pION's PAMPA Evolution Software. The pION's PAMPA-BBB includes the brain sink buffer (BSB), the BBB-1 Lipid Solution and the Stirwell™ PAMPA Sandwich plate, preloaded with magnetic disks. 4 μL of lipid were transferred in the acceptor well, followed by addition of 200 μL of BSB (pH 7.4). Then, 180 μL of diluted test compound (15-250 μM in system buffer at pH 7.4 from a 10 mM DMSO solution) was added to the donor wells. The PAMPA sandwich plate was assembled and placed on the Gut-Box™ and stirred with 60 μm Aqueous Boundary Layer (ABL) settings for 1 hour. The distribution of the compounds in the donor and acceptor buffers (150 μL aliquot) was determined by UV spectra measurement from 200 to 500 nm using the Tecan infinite M-1000 pro microplate reader. Then the Permeability ($P_{app}$, $10^{-6}$ cm/s) of each compound was calculated by the pion PAMPA evolution software. Experiments were repeated three times.

PAMPA-GIT Assay.

The PAMPA-GIT assay procedure was realized by using a method developed by pION. All liquid handling steps for the PAMPA assay are performed on a TECAN Fredom EVO150 robot and analyzed by the pION's PAMPA Evolution Software. The pION's GIT PAMPA includes the acceptor sink buffer (ASB), the GIT-0 Lipid Solution and the Stirwell™ PAMPA Sandwich plate, preloaded with magnetic disks. 4 μL of lipid were transferred in the acceptor well, followed by addition of 200 μL of ASB (pH 7.4). Then, 180 μL of diluted test compound (50-250 μM in system buffer at pH 5.0, 6.2, and 7.4 from a 10 mM DMSO solution) was added to the donor wells. The PAMPA sandwich plate was assembled and placed on the Gut-Box™ and stirred with 40 μm ABL settings for 30 min. The distribution of the compounds in the donor and acceptor buffers (150 μL aliquot) was determined by UV spectra measurement from 200 to 498 nm using the Tecan infinite M-1000 pro microplate reader. Then the Permeability ($P_{app}$, $10^{6}$ cm/s) of each compound was calculated by the pion PAMPA evolution software. The assays were repeated three times.

Antitumor Studies in Nude Mice.

Male athymic nude mice (NCr-nu), 8-12 weeks old, were provided by the Shanghai Bikai Experimental Animal Center, with the license number SCXK (Hu) 2008-0016, and maintained under specific-pathogen-free conditions. All animal protocols were approved by the Institutional Animal Use and Care Committee. All the experiments and animal care were approved by Shanghai Medical Experimental Animal Care Commission and in accordance with the Provision and General Recommendation of Chinese Experimental Animals Administration Legislation.

A549 cells were harvested, resuspended in PBS, and injected subcutaneously into 4-6 weeks old Male BALB/c nude mice. When the tumors reach an average size of 100 $mm^3$, the mice were then randomized divided into four treatment groups: Control (PBS), C-225 (40 mg/kg), M-2-5 (10 mg/kg) and M-2-5 (50 mg/kg). Mice were injected through the intraperitoneal every two days for seven injections, six days after injection, the mice in each group were killed, and the tumors were removed for examination. The tumor volumes were determined by measuring length (l) and width (w) and calculating volume ($V=lw^2/2$).

For the detection of phosphorylated EGFR, AKT and ERK in tumors in vivo, a portion of the tumor (80 mg) was immersed in 500 μL extraction buffer (50 mM Tris-HCl (pH 7.4), 150 mM NaCl, 1% NP-40, 0.25% Na-deoxycholate, Protease Inhibitor, SDS 0.1-2%), and tubes were vortexed briefly. The supernatant was transferred to a new tube and samples were centrifuged at 14,000 rpm for 15 min at 4° C. to remove any remaining insoluble material. The supernatant containing soluble proteins was transferred to a new tube and an aliquot was taken for the quantification and the further western blot analysis.

For the immunohistochemical analysis, the hydrated paraffin section was incubated in a blocking solution (10% donkey serum+5% nonfat dry milk+4% BSA+0.1% Triton X-100) for 10 min, and then incubated at 4° C. overnight with anti-P-EGFR, P-AKT, P-ERK. After washing with PBS, the sections were incubated with diluted (1:200) biotinylated secondary antibody for 30 min. Subsequently, the sections were washed again in PBS and incubated for 30 min with the preformed avidin-horseradish peroxidase macromolecular complex. Development of peroxidase reaction was achieved by incubation in 0.01% 3, 3-diaminobenzidine tetrahydrochloride (DAB) in PBS containing 0.01% hydrogen peroxide for approximately 5 min at room temperature. Sections were then washed thoroughly in tap water, counterstained in haematoxylin, dehydrated in absolute alcohol, cleared in xylene and mounted in synthetic resin for microscopic examination.

Molecular Docking Methods:

The three-dimensional structure of the molecule M-2-5 was constructed using RDKit package. The conformational search of M-2-5 was carried out using mixed torsional/low-mode sampling as implemented in Schrödinger (2015) with AMBER force field. The default parameters were used for the rest of settings. The protein complex, showing the structure of the extracellular domain of the epidermal growth factor receptor in complex with the Fab fragment of cetuximab (PDB: 1YY9), was selected for docking. After removed waters, cofactors, oligosaccharides, salt anion, metal ions, or redundant chains using PyMol, 1YY9 was prepared using Schrödinger Protein Preparation Wizard with default settings. Grid was generated using centroid of the interaction surface as the center for each crystal structure. The docking was performed using the Glide module in Schrödinger (2015) with default parameters.

What is claimed is:

1. A compound M-2-5 having the structure:

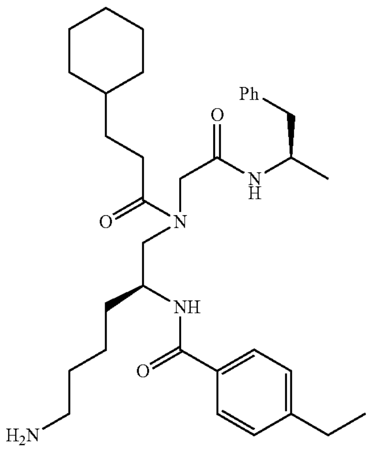

-continued

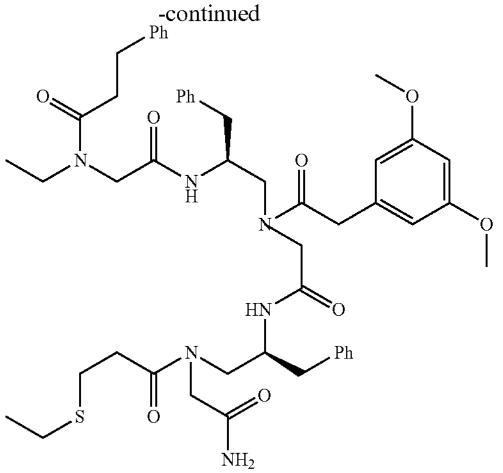

or a pharmaceutically acceptable salt thereof.

2. A pharmaceutical composition comprising a compound of claim 1, or a pharmaceutically acceptable salt thereof, and at least one pharmaceutically acceptable excipient.

* * * * *